(12) United States Patent
Ohishi

(10) Patent No.: US 11,395,601 B2
(45) Date of Patent: Jul. 26, 2022

(54) MEDICAL IMAGE PROCESSING APPARATUS

(71) Applicant: Toshiba Medical Systems Corporation, Otawara (JP)

(72) Inventor: Satoru Ohishi, Otawara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 1385 days.

(21) Appl. No.: 14/869,142

(22) Filed: Sep. 29, 2015

(65) Prior Publication Data

US 2016/0015279 A1 Jan. 21, 2016

Related U.S. Application Data

(63) Continuation of application No. PCT/JP2014/059359, filed on Mar. 28, 2014.

(30) Foreign Application Priority Data

Mar. 29, 2013 (JP) .............................. JP2013-074225

(51) Int. Cl.
  *A61B 5/026* (2006.01)
  *A61B 6/03* (2006.01)
  (Continued)

(52) U.S. Cl.
  CPC ............... *A61B 5/026* (2013.01); *A61B 5/72* (2013.01); *A61B 5/742* (2013.01); *A61B 5/743* (2013.01);
  (Continued)

(58) Field of Classification Search
  CPC ......... G06T 7/11; G06T 17/005; G06T 7/136; G06T 7/187; G06T 2207/20044; G06T 2207/10016; G06T 2207/30172
  See application file for complete search history.

(56) References Cited

U.S. PATENT DOCUMENTS

2001/0031920 A1* 10/2001 Kaufman ............... G06T 15/08
  600/431
2003/0099386 A1* 5/2003 Schneider .............. G06K 9/342
  382/130

(Continued)

FOREIGN PATENT DOCUMENTS

JP 2006-175213 A 7/2006
JP 2008-012291 A 1/2008

(Continued)

OTHER PUBLICATIONS

Office Action dated Oct. 18, 2016 in Japanese Application No. 2013-074225.

(Continued)

*Primary Examiner* — Amelie R Davis
*Assistant Examiner* — Helene Bor
(74) *Attorney, Agent, or Firm* — Oblon, McClelland, Maier & Neustadt, L.L.P.

(57) ABSTRACT

According to one embodiment, a medical image processing apparatus includes an acquiring unit, an identifying unit, and a display controller. The acquiring unit acquires volume data indicating the state of a three-dimensional region including a mass portion and a plurality of blood vessels derived from the mass portion in a subject. The identifying unit specifies a region corresponding to the mass portion and the blood vessels in the volume data as a region of interest. The identifying unit identifies the mass portion and each of the blood vessels in the region of interest. The display controller assigns a different display mode to at least one of the mass portion and the blood vessels.

15 Claims, 18 Drawing Sheets

(51) Int. Cl.
*A61B 6/00* (2006.01)
*A61B 5/00* (2006.01)
*G06T 7/11* (2017.01)
*G06T 7/136* (2017.01)
*G06T 7/187* (2017.01)
*G06T 7/00* (2017.01)
*A61B 8/06* (2006.01)
*A61B 8/00* (2006.01)
*A61B 8/08* (2006.01)
*G06T 5/30* (2006.01)
*G06T 7/66* (2017.01)
*A61B 5/055* (2006.01)

(52) U.S. Cl.
CPC .............. *A61B 6/032* (2013.01); *A61B 6/461* (2013.01); *A61B 6/504* (2013.01); *A61B 6/507* (2013.01); *A61B 6/5217* (2013.01); *A61B 8/06* (2013.01); *A61B 8/461* (2013.01); *A61B 8/5207* (2013.01); *G06T 7/0012* (2013.01); *G06T 7/11* (2017.01); *G06T 7/136* (2017.01); *G06T 7/187* (2017.01); *A61B 5/055* (2013.01); *A61B 8/0891* (2013.01); *A61B 8/483* (2013.01); *A61B 8/5223* (2013.01); *G06T 5/30* (2013.01); *G06T 7/66* (2017.01); *G06T 2207/10072* (2013.01); *G06T 2207/20104* (2013.01); *G06T 2207/30096* (2013.01); *G06T 2207/30101* (2013.01); *G06T 2207/30172* (2013.01)

(56) References Cited

U.S. PATENT DOCUMENTS

| | | | |
|---|---|---|---|
| 2003/0208116 A1* | 11/2003 | Liang | A61B 90/36 600/407 |
| 2007/0286469 A1 | 12/2007 | Yamagata et al. | |
| 2008/0170771 A1* | 7/2008 | Yamagata | G06F 19/321 382/128 |
| 2011/0237938 A1* | 9/2011 | Mizuno | G06T 7/187 600/425 |
| 2013/0034287 A1 | 2/2013 | Itagaki et al. | |
| 2014/0316758 A1* | 10/2014 | Yagi | A61B 5/026 703/9 |
| 2014/0355858 A1* | 12/2014 | O'Dell | G06T 7/11 382/131 |

FOREIGN PATENT DOCUMENTS

| | | |
|---|---|---|
| JP | 2008-194456 A | 8/2008 |
| JP | 2008-307145 A | 12/2008 |
| JP | 2010-194046 A | 9/2010 |
| JP | 2011-045448 A | 3/2011 |
| JP | 2011-92263 A | 5/2011 |
| JP | 2011-212314 A | 10/2011 |
| JP | 2011212314 A * | 10/2011 |
| JP | 2011-254861 A | 12/2011 |
| JP | 2011254861 A * | 12/2011 |
| WO | WO 2011/132593 A1 | 10/2011 |

OTHER PUBLICATIONS

English translation of the International Search Report dated Jun. 10, 2014 in PCT/JP2014/059359 filed Mar. 28, 2014.

\* cited by examiner

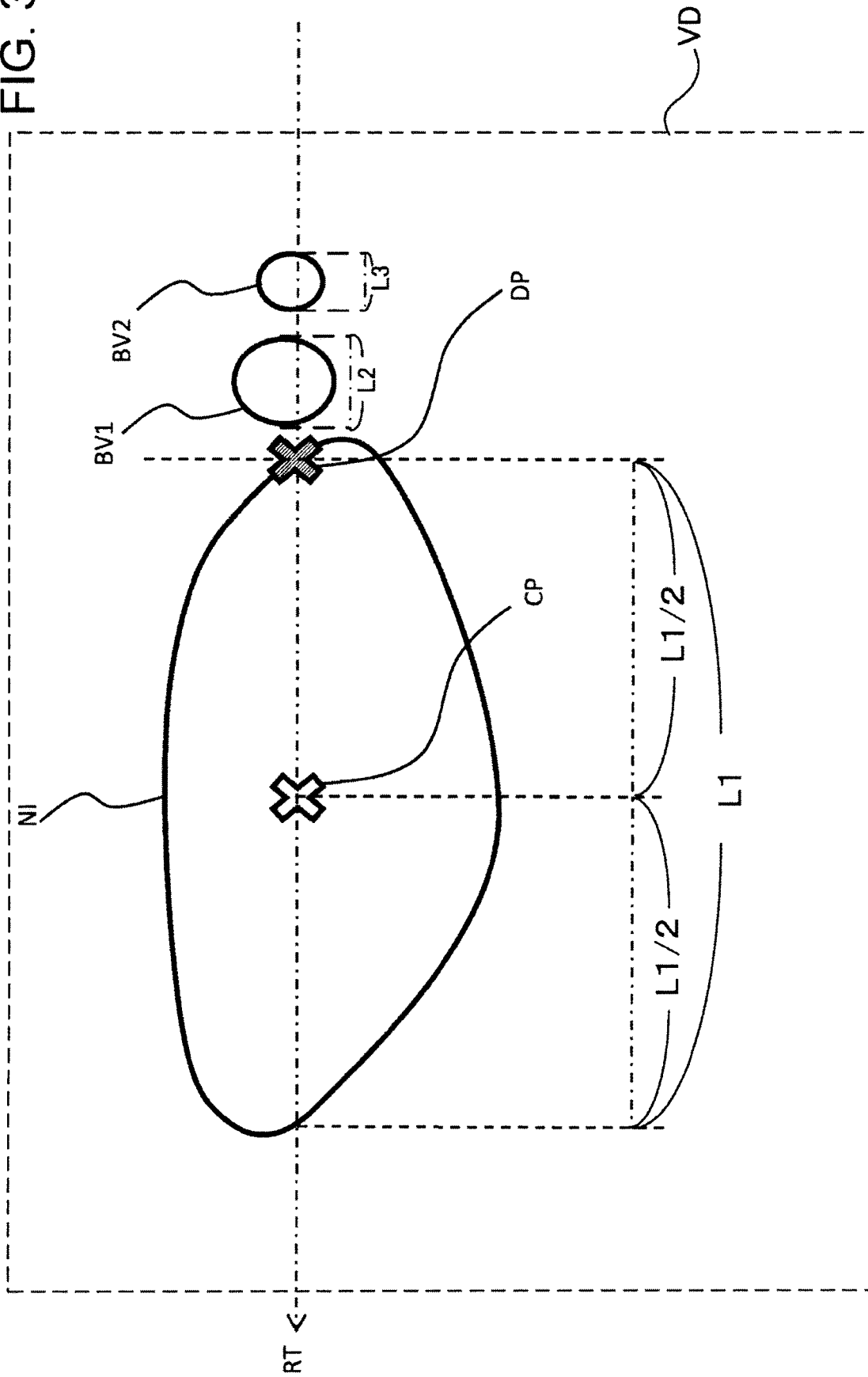

FIG. 4B
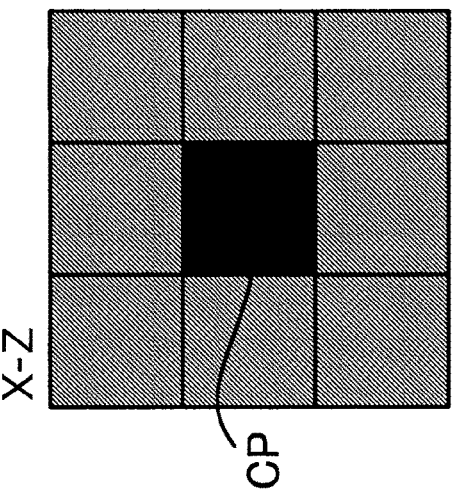
X-Z
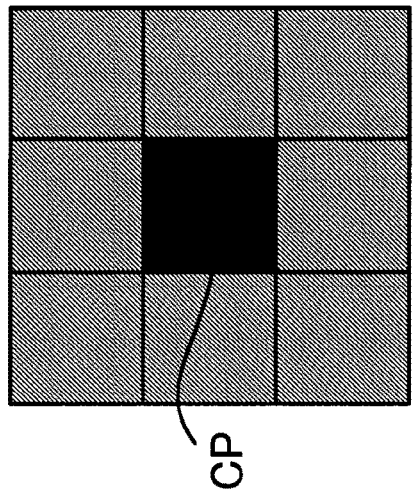
Y-Z
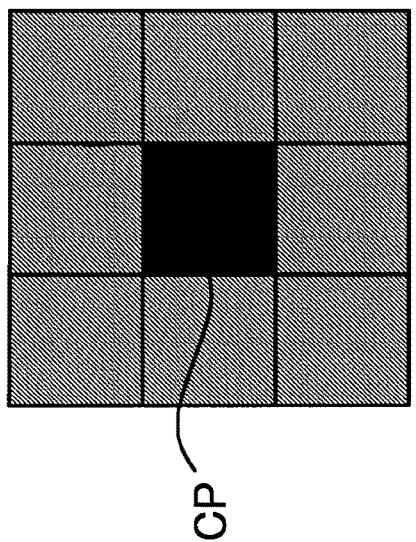
X-Y
STEP NUMBER = 1
CP
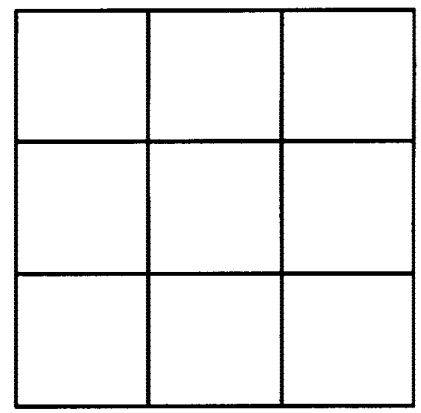
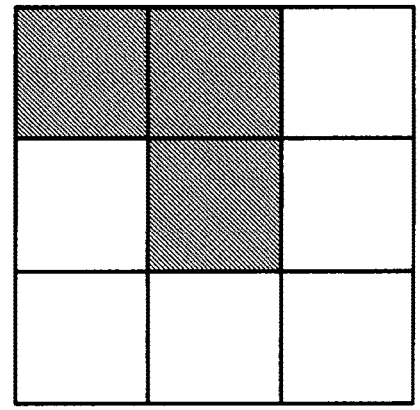
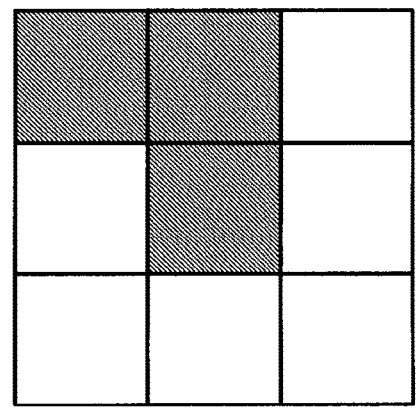
STEP NUMBER = n/2

MEDICAL IMAGE PROCESSING APPARATUS

CROSS-REFERENCE TO RELATED APPLICATION

This application is based upon and claims the benefit of priority from Japanese Patent Application No. 2013-074225, filed 29 Mar. 2013; the entire contents of which are incorporated herein by reference.

FIELD

Embodiments described herein relate generally to a medical image processing apparatus.

BACKGROUND

Interventional therapy (endovascular treatment) is performed by the medical imaging technology using an X-ray diagnostic apparatus. For example, the X-ray diagnostic apparatus generates and displays images of the inside of a subject along with the interventional therapy performed by a doctor or the like.

That doctor or the like guides a catheter inserted into the subject to a predetermined site in the subject while referring to blood vessels in an image displayed. In one example of the method of treating an aneurysm, the doctor inserts a guide wire from groin region of a leg or the like. Then, the doctor guides a catheter along the guide wire to the diseased area. The doctor embolizes a predetermined site referring to the image. The embolization is performed by, for example, placing an occlusion material such as a coil or the like in the predetermined site from the tip of the catheter. Incidentally, the site to be embolized is an aneurysm, an inflow blood vessel to an arteriovenous malformation (AVM), an inflow blood vessel to a tumor, or the like.

Blood flow to the site is blocked by this embolization. In the treatment of AVM, by occluding blood vessels flowing into a nidus, blood flow to the nidus is interrupted. Such embolization enables the direction of the blood flow to be optimized. Besides, the aneurysm is treated by placing a coil to coagulate the blood in the aneurysm. In the case of tumor therapy, by occluding blood vessels flowing into the feeding arteries that flow into the tumor, blood flow to the tumor can be shut off.

As described above, a doctor performs the embolization for shutting inflow off to a predetermined site with reference to a medical image. Therefore, it is desirable that the doctor be able to smoothly figure out the inflow blood vessels and the surrounding area thereof. In this respect, there have been proposed technologies for facilitating the recognition of the inflow blood vessel portion in medical images.

However, the feeding arteries to a tumor, the inflow blood vessels to AVM, the outflow blood vessels from the neck or dome of an aneurysm, and the like have a complex shape, and are difficult to be identified. Therefore, it has been difficult to produce a medical image that allows a viewer of the image to smoothly figure out the shape of the blood vessel in a relevant part with the medical image diagnostic apparatus.

BRIEF DESCRIPTION OF THE DRAWINGS

FIG. 3 is a schematic diagram conceptually illustrating how an identifying unit identifies the center point based on a designated point;

FIG. 4B is a schematic diagram illustrating region growing by the identifying unit;

DETAILED DESCRIPTION

In general, according to one embodiment, a medical image processing apparatus includes an acquiring unit, an identifying unit, and a display controller. The acquiring unit acquires volume data indicating the state of a three-dimensional region including a mass portion and a plurality of blood vessels derived from the mass portion in a subject. The identifying unit specifies a region corresponding to the mass portion and the blood vessels in the volume data as a region of interest. The identifying unit identifies the mass portion and each of the blood vessels in the region of interest. The display controller assigns a different display mode to at least one of the mass portion and the blood vessels.

With reference to FIGS. 1 to 17, a description is given of a medical image processing apparatus or an image acquiring device according to first to fifth embodiments.

First Embodiment

Medical Image Processing System

Figure 1:
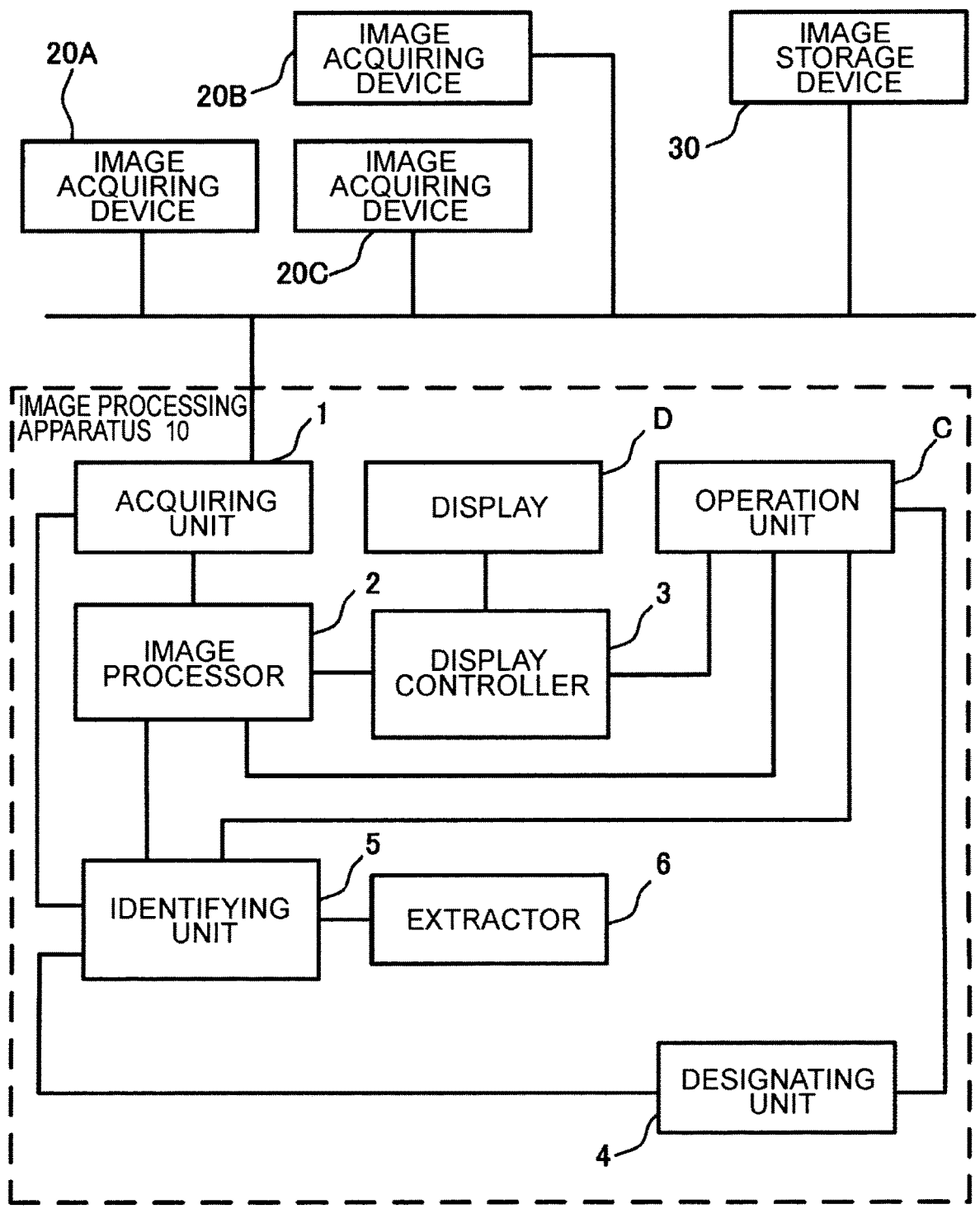
FIG. 1 is a block diagram of an image processing apparatus according to a first embodiment.

With reference to FIG. 1, a description is given of a medical image processing system according to the first embodiment. FIG. 1 is a schematic block diagram illustrating a configuration of the medical image processing system of the first embodiment. As illustrated in FIG. 1, the medical image processing system includes an image processing apparatus 10, image acquiring devices 20A, 20B, 20C, . . . , and 20n, and an image storage device 30, which are connected via a network N to be capable of data communication with one another. Although FIG. 1 illustrates the image acquiring devices 20A, 20B, 20C and the image storage device 30, which are connected to the network, this is by way of example. The number of the devices may be arbitrarily set.

For example, the image processing apparatus 10 and the image acquiring devices 20A, 20B, 20C, . . . , and 20n can transmit and receive a plurality of tomographic images or volume data via the network. The image storage device 30 stores a tomographic image or volume data generated by the image acquiring devices 20A, 20B, 20C, . . . , and 20n together with demographic information. Upon receipt of a request from the image processing apparatus 10, the image storage device 30 sends volume data and the like stored therein to the image processing apparatus 10.

In the following example, the image acquiring device 20A and the like is described as a medical image acquiring device configured to acquire information on the body tissues of a subject. Examples of the device include an X-ray image acquiring device (X-ray Angio system), an X-ray CT image acquiring device, an MRI image acquiring device, an ultrasonic image acquiring device, and the like.

Besides, for example, the image storage device 30 is of the picture archiving and communication system (PACS). For example, the image storage device 30 is an image management device that includes an image database. The image management device manages medical image data in the image database by a program. For another example, the image storage device 30 may be a file server, such as a network attached storage (NAS), configured to store medical image data.

(Outline of the Image Processing Apparatus)

The image processing apparatus 10 of the first embodiment is described by taking a medical image workstation as an example. In the first embodiment, the image processing apparatus 10 acquires volume data related to a medical image. The image processing apparatus 10 specifies a mass portion and blood vessels derived from the mass portion in the volume data, and identifies the specified area as a region of interest. The image processing apparatus 10 of the first embodiment is configured to acquire volume data acquired in advance by the image acquiring devices 20A to 20C and stored in the image storage device 30. However, for another example, the image processing apparatus 10 may be configured to, as in the second embodiment described later, acquire information on the body tissues of a subject, and perform reconstruction process to generate volume data.

As illustrated in FIG. 1, the image processing apparatus 10 includes a display D, an operation unit C, an acquiring unit 1, an image processor 2, a display controller 3, a designating unit 4, an identifying unit 5, and an extractor 6. Described below is the configuration of each unit of the image processing apparatus 10.

(Display)

The display D is formed of any type of display device such as, for example, cathode ray tube (CRT) display, liquid crystal display (LCD), organic electroluminescence display (OELD), or field emission display (FED). The display D displays various operation screens, setting screens, and medical images under the control of the display controller 3.

(Operation Unit)

The operation unit C includes any type of operation device or input device such as, for example, a keyboard, a mouse, a trackball, a joystick, and a control panel. The operation unit C may further include the same device as the display D such as a touch panel or the like. The main controller (not illustrated) receives an operation signals that the operation unit C has output based on the operation performed thereon, and performs the operation of controlling each unit according to the operation contents.

(Acquiring Unit)

The acquiring unit 1 receives the operation signals from the operation unit C, and requests the image storage device 30 for volume data (acquisition request). For example, a user enters a patient ID or an examination ID in the image processing apparatus 10 using the operation unit C, and performs the operation related to the acquisition request for volume data. Upon receipt of the operation signals, the acquiring unit 1 requests the image storage device 30 for volume data based on the IDs entered along with the operation signals.

In response to the acquisition request, the image storage device 30 searches for the volume data. The image storage device 30 retrieves the volume data corresponding to the IDs or the like and sends it to the image processing apparatus 10. The acquiring unit 1 at least temporarily stores the volume data received from the image storage device 30. The acquiring unit 1 includes any storage medium such as, for example, a random access memory (RAM), a hard disk drive (HDD), a solid-state drive (SSD), or the like. Note that another storage device may store the volume data.

While the volume data after various processes, such as second identification process (described later), extraction process, and the like, is described as being stored in the identifying unit 5, this is not a limitation. The acquiring unit 1 may store the volume data. The acquiring unit 1 may also store a volume rendering image in the two-dimensional image processing. Further, the acquiring unit 1 stores image processing conditions for two-dimensional image processing (volume rendering, surface rendering, etc.) with respect to the volume data.

(Image Processor)

The image processor 2 performs image processing related to the generation of a two-dimensional image on the volume data according to the operation signals for image processing performed on the operation unit C. For example, when a user performs operation signals for generating a volume rendering (VR) image based on the volume data, the image processor 2 receives an instruction related to the operation signals. Upon receipt of the instruction, the image processor 2 displays, on the display D, a setting screen for setting various parameters related to volume rendering via the display controller 3. The parameters include setting information for the observation angles related to such volume rendering. The parameters also include setting information for the transparency of the voxel value in the volume data. The parameters further include setting information for the window level (WL) and window width (WW) in the volume rendering image.

When the user sets various parameters on the setting screen using the operation unit C, the parameters are sent to the image processor 2. The image processor 2 performs a process for generating a volume rendering image based on the parameters. For example, the image processor 2 determines the observation angles of the image and the position of the light source in the volume rendering according to the observation angles. The image processor 2 sets the transparency of voxels according to the transparency set with respect to voxel values.

In this manner, the image processor 2 performs volume rendering on the volume data to thereby generate a two-dimensional image. The image processor 2 need not necessarily be configured to generate a volume rendering image based on parameters set by the user. For example, the image processor 2 may generate a volume rendering image using data set in advance as at least a part of the parameters. Incidentally, in the process of the following embodiments, the two-dimensional image generated by any one of the above approaches contains, for example, the surface shapes of an aneurysm and an outflow blood vessel from the aneurysm, a nidus of an arteriovenous malformation (AVM) and an inflow blood vessel to the nidus, a tumor and an inflow blood vessel to the tumor, or the like.

The image processor 2 sends the volume rendering image thus generated to the display controller 3. The image processor 2 stores the parameters for the observation angles and the like used in the volume rendering in association with the target volume data. While the image processor 2 is described above as being configured to generate a volume rendering image, this is not a limitation. For example, the image processor 2 may generate a surface rendering image, a maximum-intensity projection (MIP) image, a minimum intensity projection (MinIP) image, and the like.

(Display Controller)

The display controller 3 generates a setting screen for various parameters related to the generation of the two-dimensional image by the image processor 2, and controls the display D to display it. The display controller 3 controls the display D to display the volume rendering image generated by the image processor 2. Further, the display controller 3 controls the display D to display a medical image containing a blood vessel region extracted, or a mass region and a blood vessel region. The extraction of a blood vessel region or the like is described later. The display controller 3 controls the display D to display the setting screen related to the display mode of the blood vessel region and the like. Note that it is assumed hereinbelow that each image is displayed on the display D as a result of display control by the display controller 3, unless otherwise specified.

As a control example, the display controller 3 controls the display D to display a volume rendering image. While the volume rendering image is being displayed, the image processing apparatus 10 can receive operation signals for designating a point (designated point) described below. It is assumed in this embodiment that a mass portion is illustrated in the volume rendering image. The mass portion is, for example, a nidus in AVM, an aneurysm, a tumor, or the like. It is also assumed that a blood vessel continuous with the mass portion or derived from the mass portion is illustrated in the volume rendering image. Besides, in the following, among the tissues in the subject, a mass portion representing a nidus, an aneurysm, a tumor or the like may be simply referred to as "mass portion". Also, the blood vessel continuous with the mass portion or derived from the mass portion may be simply referred to as "derived blood vessel".

In addition, the display controller 3 may control the display D to display a message prompting a user to designate a part of the mass portion, for example, a point in a range indicating a mass portion in the image. The display controller 3 may be configured to determine whether the volume rendering image contains a region representing a mass portion.

For example, the display controller 3 stores a range of pixel values representing a blood vessel and a mass portion. The display controller 3 also stores information on the size of the mass portion relative to other portions (bone, etc.). The display controller 3 obtains a range occupied by pixels having a pixel value indicating the mass portion or the like in the volume rendering image based on the information stored. Besides, the display controller 3 obtains the size of the range based on the number of pixels or the like. The display controller 3 compares the size of the mass portion stored with the size of the range obtained. As a result of the comparison, when the relative size of the mass portion does not reach the stored size, the display controller 3 may control the display D to display a warning message or the like indicating that the displayed volume rendering image contains no mass portion.

(Designating Unit)

When operation is performed to set a designated point on the operation unit C while the volume rendering image is being displayed on the display D, the designating unit 4 receives the operation. The designated point is used in the process of identifying the center point by the identifying unit 5 (described later). For example, if a user designates a position corresponding to the center position of the mass portion indicated in volume rendering image using the user operation unit C, the designating unit 4 stores the coordinates corresponding to the designated position in the image as the designated point. Further, when the user performs operation for determining the designated point, the designating unit 4 sends coordinate information of the designated point to the identifying unit 5.

Although the designating unit 4 is described above as being configured to store a position in the image designated by the user as the designated point, this embodiment is not so limited. For example, if the display controller 3 is configured as described above to identify the range of the mass portion or the like in the image, the designating unit 4 acquires the coordinates of a region indicating the mass portion in the image or the coordinates of the contour thereof. Further, the designating unit 4 obtains the coordinates corresponding to the center point based on information about a portion indicating the contour received from the display controller 3. The designating unit 4 may be configured to store the coordinates of the center point obtained as the designated point. In this configuration, the designated point may be moved by the user through the operation unit C to be editable.

(Identifying Unit)

Figure 2:
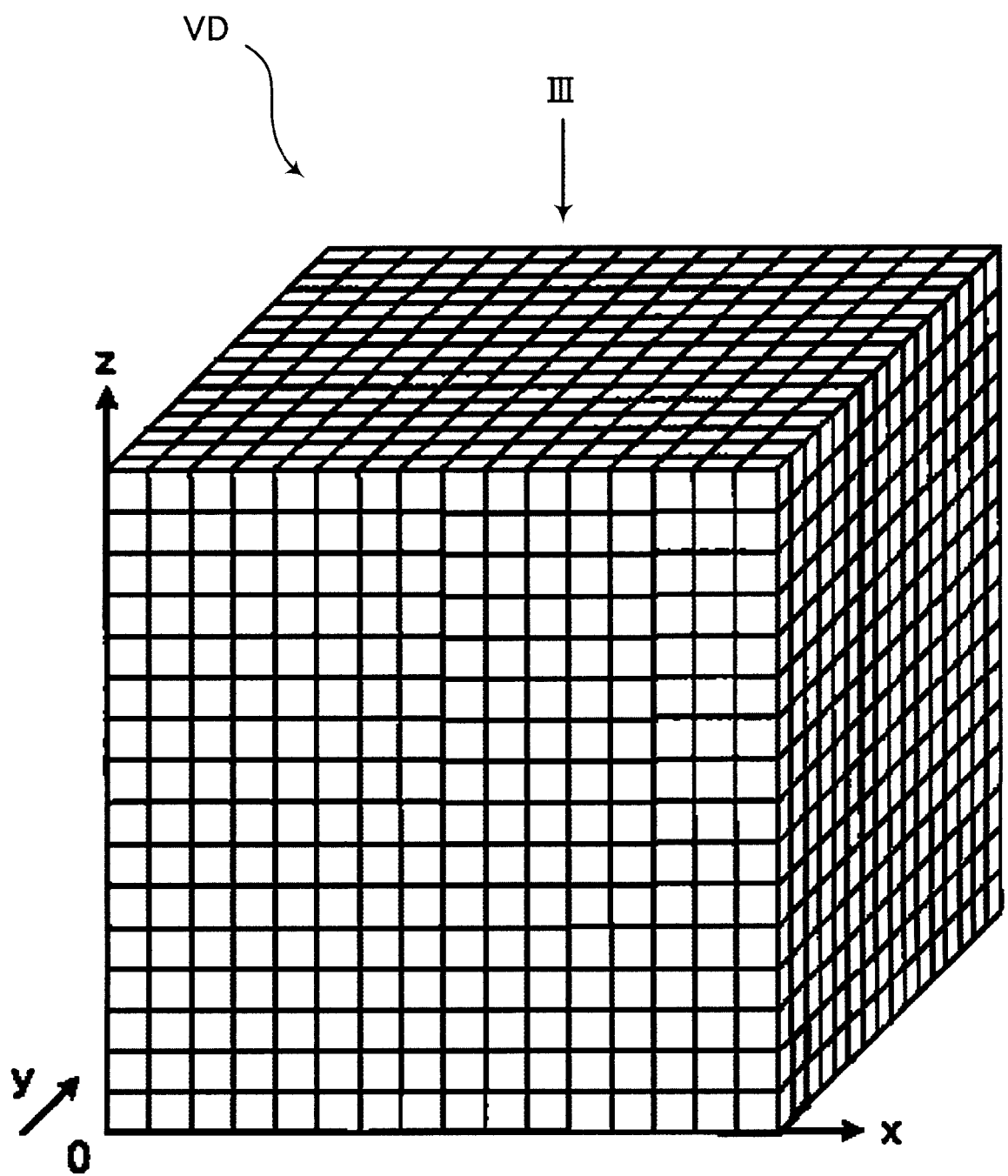
FIG. 2 is a schematic diagram conceptually illustrating volume data.
Figure 4A:
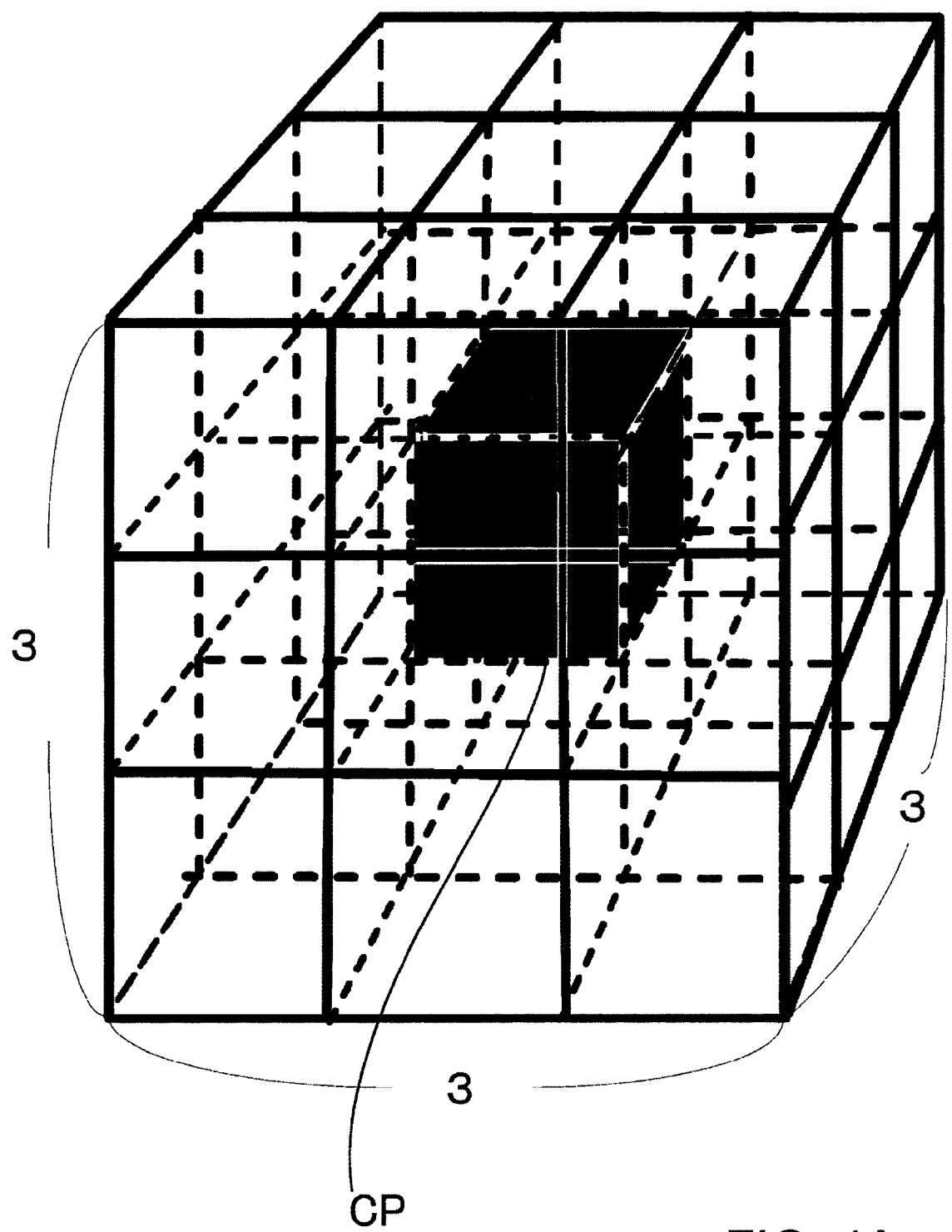
FIG. 4A is a schematic diagram conceptually illustrating region growing by the identifying unit.
Figure 5:
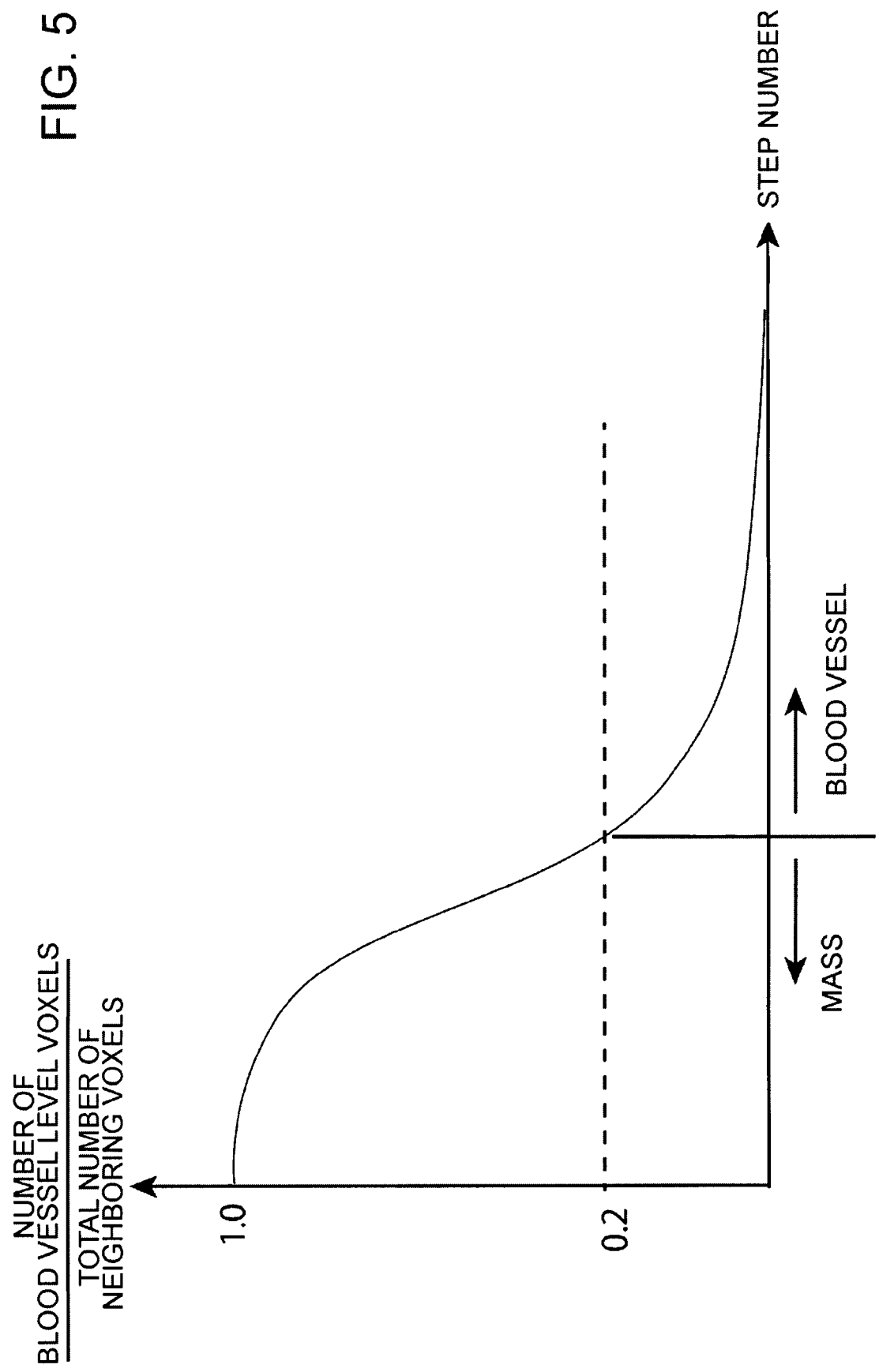
FIG. 5 is a graph schematically illustrating a relationship between the step number of region growing and the ratio of target region voxels to all neighboring voxels.

The identifying unit is described below with reference to FIGS. 1 to 5. FIG. 2 is a schematic diagram conceptually illustrating volume data. FIG. 3 is a schematic diagram conceptually illustrating how the identifying unit 5 identifies the center point based on the designated point. FIGS. 4A and 4B are schematic diagrams conceptually illustrating the region growing by the identifying unit 5. FIG. 5 is a graph schematically illustrating a correspondence relationship between the step number of region growing and the ratio of target region voxels to all neighboring voxels. In the following description, identification process is classified into first identification process as a process of identifying the center point and second identification process as a process of identifying the mass portion and the derived blood vessel. Note that the center point to be described below may be, but not necessarily be, the center of an actual mass portion. That is, in this embodiment, a point in volume data identified in the first identification process is referred to as "center point" or "designated point" for convenience.

(First Identification Process)

With reference to FIG. 2, the first identification process is described. The identifying unit 5 receives information related to the coordinates of the designated point in a volume rendering image from the designating unit 4. Accordingly, the identifying unit 5 acquires the volume rendering image related to the designation of the designated point. The identifying unit 5 acquires volume data related to the volume rendering image from the acquiring unit 1. Further, the identifying unit 5 acquires the image processing conditions for two-dimensional image processing (volume rendering, surface rendering, etc.) with respect to the volume data stored in the acquiring unit 1.

The identifying unit 5 obtains the correspondence relationship between the volume rendering image and the volume data based on the image processing conditions acquired, the coordinates of the volume rendering image and those of the volume data. That is, the identifying unit 5 determines a voxel in the volume data, to which each pixel of the volume rendering image corresponds.

Next, the identifying unit 5 obtains the coordinates of the designated point in the volume data based on the correspondence relationship between the coordinates of the designated point in the volume rendering image and those of the voxel of the volume data. Further, the identifying unit 5 extracts the observation angle (projection direction) of the image with respect to the volume data in the volume rendering from the image processing conditions of the volume rendering image acquired from the acquiring unit 1. When the image processing conditions do not include information on the observation angle of the volume rendering image, the identifying unit 5 obtains the observation angle based on the correspondence relationship between the display content of the volume rendering image and the volume data.

Then, the identifying unit 5 obtains a trajectory RT passing through the designated point in the volume data in the observation angle. This process is described with reference to FIGS. 2 and 3. FIG. 2 illustrates volume data three-dimensionally. FIG. 3 illustrates an X-Y cross section perpendicular to the Z-axis direction in FIG. 2. That is, the cross-section of FIG. 2 is perpendicular to the volume rendering image perpendicular to the Y-axis direction and along the X-axis direction and the Z-axis direction. In other words, assuming that the direction (Y direction) in which the volume rendering image is viewed from the observation angle corresponds to the front of the volume data, FIG. 3 is a conceptual diagram of the volume data viewed from the bottom to the top and vice versa.

As illustrated in FIG. 3, the identifying unit 5 obtains a trajectory RT that passes through a designated point DP along the observation angle (lateral direction in FIG. 2) in volume data VD. Then, the identifying unit 5 extracts the voxel value of each of voxels that the trajectory RT has passed through with the coordinates of the voxel. The identifying unit 5 retrieves the setting information of a predetermined voxel value stored in advance. The setting information includes a voxel value indicating a mass portion and a voxel value indicating a blood vessel. The identifying unit 5 compares the setting information of the voxel value retrieved and the voxel value of each of voxels that the trajectory RT has passed through. By this comparison, the identifying unit 5 determines a region corresponding to a mass portion on the trajectory RT, a region corresponding to a blood vessel, and the other regions.

Incidentally, the voxel value related to the setting information may have a predetermined range. Besides, the region corresponding to a mass portion and the region corresponding to a blood vessel determined here correspond to an example of "region of interest", and the other regions correspond to an example of "other parts". Further, the setting information corresponds to an example of "threshold to identify voxels corresponding to a mass portion or a blood vessel". At this point, it has not been determined whether the region corresponding to the blood vessel is of a blood vessel derived from the mass portion.

As a result of the comparison, the identifying unit 5 obtains the coordinates of voxels having a voxel value corresponding to the setting information among the voxels that the trajectory RT has passed through. Further, the identifying unit 5 obtains the widths L1, L2, L3, . . . , and Ln of a portion where voxels corresponding to the setting information continue on the trajectory RT. The identifying unit 5 determines the largest one of the widths L1, L2, L3, . . . , and Ln as a mass portion. In FIG. 2, the width L1 is the widest. Further, the identifying unit 5 obtains the coordinates of a middle position of the largest width L1 determined as a mass portion based on the coordinates of the beginning and the end of L1 (L1/2). In this manner, the identifying unit 5 identifies the middle position obtained as the center point of the mass portion (see FIG. 3, reference sign CP).

Note that the identifying unit 5 may obtain the size of the other mass portion relative to other sites (bone, etc.). Furthermore, the identifying unit 5 compares the largest width L1 with the size of the other mass portion relative to other sites (bone, etc.). As a result of the comparison, when the largest width L1 does not reach the relative size, the display controller 3 may perform display control to prompt a user to enter the designated point again. Alternatively, the display controller 3 may perform display control to display a warning message or the like indicating that the image contains no mass portion.

(Second Identification Process)

Next, with reference to FIGS. 3, 4A and 4B, a description is given of the second identification process performed by the identifying unit 5 for identifying a mass portion and a derived blood vessel. As the second identification process, an example is described in which the region of a mass portion is iteratively extended to reach a derived blood vessel by the region growing. In this example, as for a range to be extended by one step of the region growing, two voxels are added along the X-axis, the Y-axis, and the Z-axis around the center point CP identified in the first identification process. Specifically, in the following description, the identifying unit 5 appends the region of 26 voxels around the center voxel, which is obtained by subtracting one center voxel from the region of 3 voxels in the X-axis, the Y-axis, and the Z-axis, i.e., 3×3×3=27 voxels.

FIG. 4A conceptually illustrates a process of adjacent 26 voxels around the center point CP identified in the first identification process by one step of the region growing. FIG. 4B conceptually illustrates, in the upper part, the growing range with respect to each of the X-axis, the Y-axis, and the Z-axis including the center point CP. FIG. 4B also illustrates, in the lower part, the ratio of a mass portion or a derived blood vessel to other parts when a half of the total steps n of the region growing has been performed. The total step number n of the region growing described herein refers to the number of steps when the process of identifying a derived blood vessel is completed, and does not need to be determined in advance. However, the total step number of the region growing may be determined in advance as a modification described later. Incidentally, in FIGS. 4A and 4B, a hatched portion indicates a mass portion or a derived blood vessel.

In the second identification process, the identifying unit 5 also uses the setting information of the voxel value retrieved in the first identification process. That is, the setting information is a voxel value representing a mass portion or a blood vessel. In the region growing, the identifying unit 5 compares the setting information of the relevant voxel value with the voxel value of each of 26 neighboring voxels. Described below is the flow of the process of identifying a mass region and a derived blood vessel region by the region growing.

The identifying unit 5 extends the region from the center point CP while iteratively appending a connected region that has been determined to belong to the mass portion by the above comparison through the region growing. The identifying unit 5 determines the connectivity of a region based on whether it is within the range of the setting information around the center point CP as the start point.

Incidentally, the identifying unit 5 does not need to perform the region growing by comparing the setting information with the voxel value of the neighboring voxels. For example, the identifying unit 5 may change the setting information as region growing conditions according to the state of change in the voxel values of neighboring voxels in the course of the region growing process. As a specific example, the identifying unit 5 obtains a numerical value that indicates the variation in the voxel values of the neighboring voxels in the course of the region growing process (search process). The identifying unit 5 changes the setting information as region growing conditions based on the state of the numerical value that indicates the variation.

<Discrimination Between Mass Portion and Derived Blood Vessel>

Next, with reference to FIGS. 4B and 5, a description is given of the discrimination between a mass portion and a derived blood vessel in the second identification process. Having determined that, in the range determined in advance to be appended (26 neighboring voxels, etc.), most of the voxels correspond to a mass region or a derived blood vessel region, the identifying unit 5 determines that search is performed in the range of a mass portion. On the other hand, having determined that the region grows in only part of the directions in the second identification process, the identifying unit 5 determines that a search for a derived blood vessel region is started. An example of this determination is described below.

The identifying unit 5 stores in advance a threshold value of the ratio of voxels corresponding to a mass region and a derived blood vessel region (the number of blood vessel level voxels, etc.) to the total number of neighboring voxels as a boundary value between the mass portion and the derived blood vessel. As described above, when the region begins to grow in only part of the directions in the second identification process, it can be determined that the region of a derived blood vessel is reached. As to whether the region grows in only part of the directions, the identifying unit 5 makes a determination based on whether the ratio of voxels corresponding to a mass region or a derived blood vessel region to all neighboring voxels is equal to or less than the threshold value. When the ratio is equal to or less than the threshold value, the identifying unit 5 determines that the derived blood vessel region is reached in the region growing. In the example of FIG. 5, the threshold of the ratio of voxels corresponding to a mass region or a derived blood vessel region to the total number of neighboring voxels is "0.23".

In other words, the identifying unit 5 obtains the ratio of voxels corresponding to a mass region or a derived blood vessel region to the number of all neighboring voxels in each region growing step. In addition, the identifying unit 5 compares the ratio thus obtained with the threshold value. As a result of the comparison, if the ratio is equal to or less than the threshold value, the identifying unit 5 determines that the region of a derived blood vessel is reached.

<Extension of Derived Blood Vessel Region>

Described below is the process of extending a derived blood vessel region performed by the identifying unit 5. In the second identification process, having determined that any of the appending 26 voxels reached a blood vessel region as a result of the region growing, the identifying unit 5 determines whether the derived blood vessel has a branch as well as continuing the region growing.

For example, after determining that any of the appending 26 voxels reached, the identifying unit 5 performs a thinning process with respect to each region growing step set in advance. The identifying unit 5 specifies a voxel in the derived blood vessel subjected to the thinning process as the center line (axis) of the derived blood vessel. Further, having continued the region growing, the identifying unit 5 determines whether there is a branch in the center line of the derived blood vessel. When determining that there is a branch, the identifying unit 5 ends the process of extending the derived blood vessel region by the region growing. The identifying unit 5 sends coordinate information of voxels in the mass region identified and that of voxels in the derived blood vessel region identified to the extractor 6 to extract the regions from volume data.

(Extractor)

The extractor 6 receives the coordinate information of the voxels in the mass portion and the derived blood vessel identified by the identifying unit 5. Based on each piece of the coordinate information, the extractor 6 associates the voxels of the mass region in the volume data with first region information indicating the mass region. Similarly, the extractor 6 associates the voxels of the derived blood vessel region with second region information indicating the derived blood vessel region.

Upon completion of the above process, the extractor 6 sends the volume data associated with the region information to the identifying unit 5. The identifying unit 5 stores the volume data. The first region information and the second region information may be identification information such as ID. Either or both of the above processes by the identifying unit 5 and the extractor 6 correspond to an example of the process of identifying by processing circuitry.

(Image Processor; Process of Varying Display Mode)

Described below is the process of varying the display mode of the mass region or the derived blood vessel region by the image processor 2. When operation is performed for displaying an image based on the volume data that has been subjected to the above process by the extractor 6, the image processor 2 specifies the mass region and the derived blood vessel region based on the coordinate information of the first region information and that of the second region information associated with the volume data. The image processor 2 assigns a display mode set in advance to voxels in each region specified.

As the display mode, for example, display color may be set in advance. That is, the image processor 2 displays the mass region and the derived blood vessel region extracted in color (red, etc.), and other parts in grayscale. For another example, transparency is set in advance as the display mode. That is, the image processor 2 displays the mass region and the derived blood vessel region extracted as 0% transparent (100% opacity), and other parts as 80% transparent (20% opacity).

For still another example of the display mode, the image processor 2 may extract the contours of the mass region and the derived blood vessel region, and display the contours thus extracted with different color or transparency from other parts.

(Operation of the Image Processing Apparatus)

Figure 6:
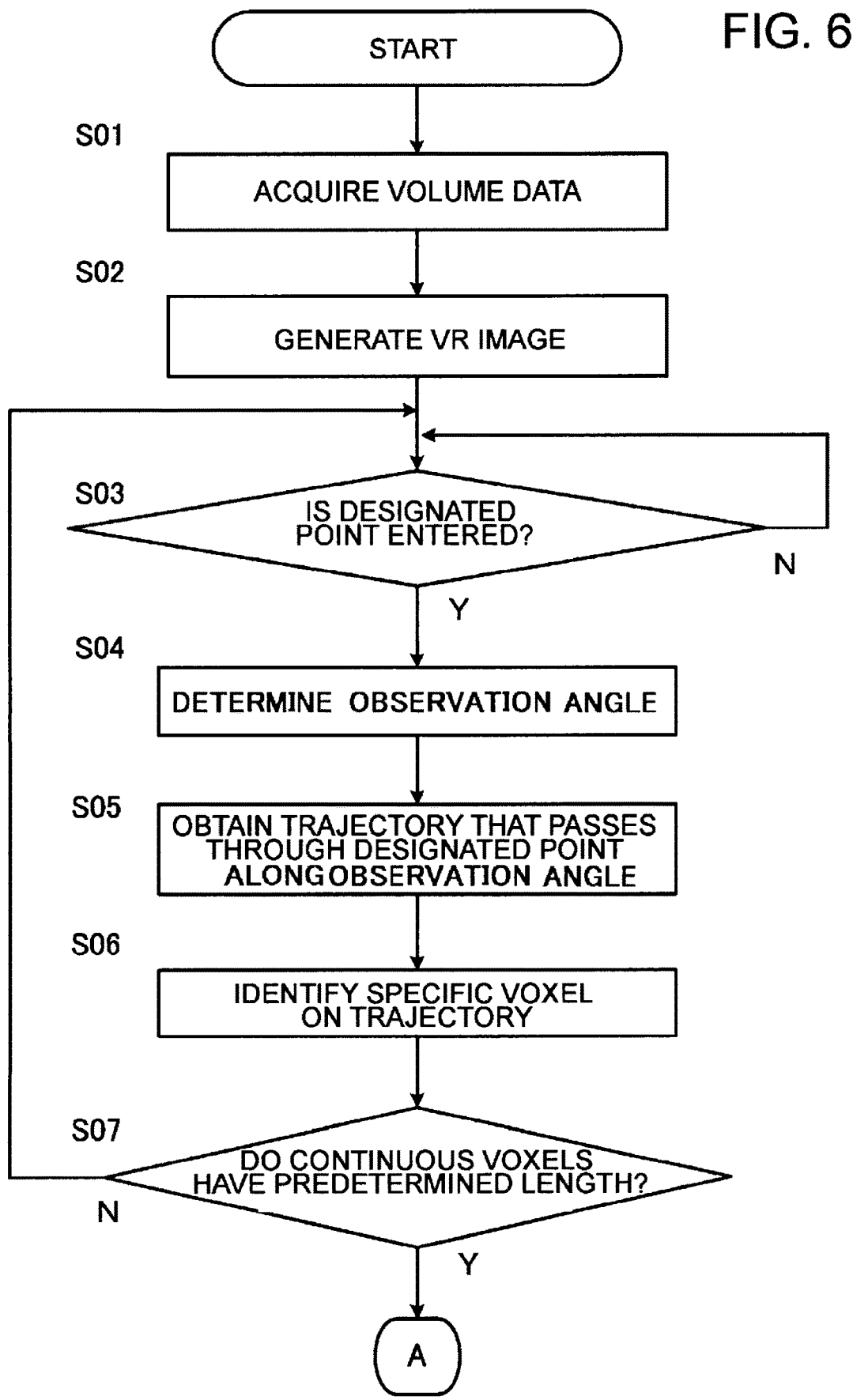
FIG. 6 is a flowchart of the operation of the image processing apparatus of the first embodiment.
Figure 7:
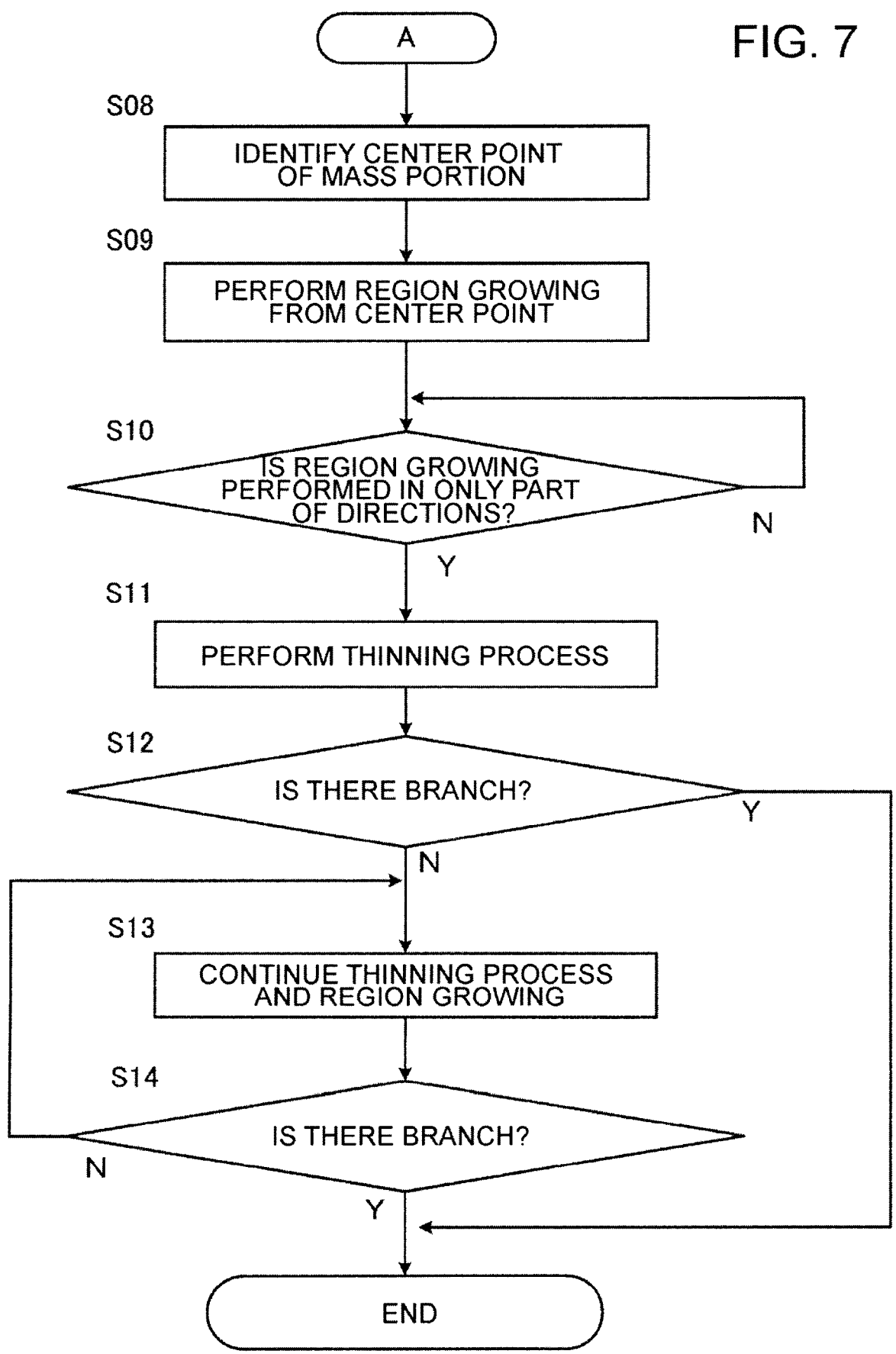
FIG. 7 is a flowchart of the operation of the image processing apparatus of the first embodiment.

Next, the operation of the image processing apparatus 10 is described with reference to FIGS. 6 and 7. FIGS. 6 and 7 are flowcharts illustrating the outline of the operation of the image processing apparatus 10 according to the first embodiment.

<Step S01>

Upon receipt of an operation signal from the operation unit C, the acquiring unit 1 requests the image storage device 30 for volume data. Consequently, the acquiring unit 1 receives the volume data from the image storage device 30, and at least temporarily stores it.

<Step S02>

In response to operation for image processing performed on the operation unit C, the image processor 2 performs image processing related to the generation of a two-dimensional image on the volume data. For example, when the user performs operation for generating a volume rendering (VR) image based on the volume data and sets various parameters such as observation angles, in response to the operation, the image processor 2 determines the position of the light source and the observation angles of the image in the volume rendering according to the observation angles. Besides, according to the setting of the transparency for the voxel values, the image processor 2 sets the transparency of voxels. In this manner, the image processor 2 performs volume rendering on the volume data to generate a pseudo three-dimensional image (two-dimensional image).

The image processor 2 sends the volume rendering image thus generated to the display controller 3. The display controller 3 controls the display D to display the volume rendering image generated by the image processor 2. Further, the display controller 3 may perform display control to prompt the user to specify part of a mass portion in the volume rendering image, for example, one point in the range indicating the mass portion in the image. The display controller 3 may be configured to determine whether the volume rendering image contains a region representing the mass portion.

<Step S03>

While the volume rendering image is being displayed on the display D, the designating unit 4 determines whether operation is performed on the operation unit C to designate a point. In addition, the designating unit 4 determines whether operation is performed for the confirmation of the designated point. The designating unit 4 repeats this determination until designation and confirmation are performed (No in step S03). Incidentally, only the designation may be performed without the confirmation. Note that, instead of user's designation, the designating unit 4 may obtain a region indicating a mass portion or the counter thereof in the image, and determines a point corresponding to the center. In this configuration, the point corresponding to the center may be editable by the user.

<Step S04>

Having determined that designation and confirmation are performed (Yes in step S03), the designating unit 4 sends the coordinate information of the designated point to the identifying unit 5. The identifying unit 5 acquires the volume rendering image related to the designation of the designated point. The identifying unit 5 also acquires volume data related to the volume rendering image from the acquiring unit 1. Further, the identifying unit 5 acquires the image processing conditions of the two-dimensional image processing for the volume data stored in the acquiring unit 1. Then, the identifying unit 5 extracts the observation angles (projection direction) of the image with respect to the volume data from the image processing condition acquired.

<Step S05>

Next, based on the observation angle determined in S04, the identifying unit 5 obtains the trajectory RT that passes through the designated point DP along the observation angle (lateral direction in FIG. 2) in the volume data VD.

<Step S06>

The identifying unit 5 compares the setting information of voxel value retrieved with the voxel values that the trajectory RT passes through. By this comparison, the identifying unit 5 identifies a region corresponding to a mass portion, a region of interest corresponding to a blood vessel, and other regions on the trajectory RT. As a result of the comparison, the identifying unit 5 obtains the coordinates of voxels with voxel values corresponding to the setting information among those that the trajectory RT passes through.

<Step S07>

The identifying unit 5 obtains the widths L1, L2, L3, . . . , and Ln of portions where voxels corresponding to the setting information continue on the trajectory RT (see FIG. 3). The identifying unit 5 determines the largest one of the widths L1, L2, L3, . . . , and Ln as a mass portion. Further, the identifying unit 5 obtains the size of the other mass portion relative to other sites (bone, etc.) to determine whether the largest width L1 reaches the relative size of the other mass portion (whether the mass portion has a predetermined size). If the largest width L1 does not reach the relative size (No in step S07), the display controller 3 performs display control to prompt a user to enter the designated point again, and the process returns to step S03. This is because the designated point may be deviated from the region of the mass portion.

<Step S08>

Having determined that the largest width L1 reaches the predetermined size (Yes in step S07), the identifying unit 5 obtains the coordinates of the middle position of L1 based on the coordinates of the beginning and the end of L1 (L1/2). In this manner, the identifying unit 5 identifies the middle position obtained as the center point CP of the mass portion.

<Step S09>

Through the region growing, the identifying unit 5 iteratively compares the setting information of the voxel value with the voxel value of each of the 26 neighboring voxels from the center point CP as a start point. A group of the 26 neighboring voxels are those set as a range for a search with respect to the center point CP. By this comparison, the identifying unit 5 performs region growing while iteratively appending a connected region that belongs to the mass portion. The identifying unit 5 determines the connectivity of a region based on whether it is within the range of the setting information around the center point CP as the start point.

<Step S10>

Along with the region growing, the identifying unit 5 determines whether the ratio of voxels corresponding to the mass region and those corresponding to the derived blood vessel region to the total number of the neighboring voxels is equal to or less than the threshold value. That is, the identifying unit 5 iteratively extends the region by the region growing until it is determined that the region grows in only part of the directions (No in step S10).

<Step S11>

Having determined that the region grows in only part of the directions (Yes in step S10), the identifying unit 5 performs a thinning process to obtain the center line of the derived blood vessel region extending in the growing direction.

<Step S12>

The identifying unit 5 determines whether there is a branch in the center line obtained in step S11.

<Step S13>

Having determined that there is no branch in the center line obtained in step S11 (No in step S12), the identifying unit 5 continues the thinning process and the region growing of the derived blood vessel region. Here, the same process as steps S09 and S11 is performed.

<Step S14>

When determining that there is no branch in the center line in step S13, the identifying unit 5 repeats steps S13 and S14.

Having determined that there is a branch (Yes in step S12/S14), the identifying unit 5 ends the thinning process and the region growing of the derived blood vessel as the second identification process.

Based on the coordinate information obtained by the identification process, the extractor 6 associates the corresponding voxel with the first region information (mass region) and the second region information (derived blood vessel region). The extractor 6 sends the volume data associated with the region information to the identifying unit 5. The identifying unit 5 stores the volume data.

When operation is performed for displaying an image based on the volume data subjected to the above process, the image processor 2 specifies the mass region based on the coordinate information of the first region information associated with the volume data. In addition, the image processor 2 specifies a derived blood vessel region based on the coordinate information of the second region information. The image processor 2 assigns a display mode set in advance to voxels in each region specified.

According to the first embodiment, the image processing apparatus 10 acquires volume data including a mass portion and blood vessels derived from the mass portion. The image processing apparatus 10 generates a volume rendering image from the volume data. The image processing apparatus 10 receives an input of a designated point of the volume rendering image. Based on the designated point of the volume rendering image, the image processing apparatus 10 identifies a voxel (or a group of voxels) which is assumed to be the center point of the mass portion in the volume data. The image processing apparatus 10 performs region growing from the center point as the start point, and identifies a derived blood vessel region. The image processing apparatus 10 associates voxels identified in the volume data with information indicating the mass portion or the derived blood vessel.

With this configuration, an object in the volume data can be identified even if it has a complex shape like feeding arteries to a tumor, an inflow blood vessel to AVM, an outflow blood vessel from the neck or dome of an aneurysm, and the like. Thus, the image processing apparatus 10 can distinguishably display a mass portion and a derived blood vessel identified in a medical image, thereby improving the visibility of the objects.

(Modification 1)

According to the first embodiment, after the derived blood vessel region is reached as a result of the region growing in the second identification process, the thinning process is performed for each predetermined number of steps of the region growing. Then, it is determined whether there is a branch. However, this embodiment is not limited to this. For example, the identifying unit 5 may be configure to end the region growing after extending the region by a predetermined distance set in advance from the center point CP without a determination as to whether the derived blood vessel region is reached to a branch. That is, the identifying unit 5 may perform region growing only without performing steps S10, S12 and S14 illustrated in FIG. 7. Alternatively, in this modification 1, the identifying unit 5 may determine whether the derived blood vessel region is reached, but not determine whether there is a branch (steps S12 and S14). In the modification 1, the predetermined distance is stored in advance.

In the sense of the end timing of the region growing, the mass portion and the derived blood vessel can be identified in the modification 1. For example, the predetermined distance is set in advance based on the size of a site to be examined in the subject, the distance to the derived blood vessel from the center point CP of the mass portion obtained by statistics, and the like. Incidentally, the region growing may be performed by a predetermined number of steps, instead of by the predetermined distance. This is because if the distance from the center point CP of the mass portion to the derived blood vessel can be assumed, the number of steps to reach the derived blood vessel can also be assumed.

Accordingly, with this configuration, an object with a complex shape can be identified in volume data. Thus, the image processing apparatus 10 can distinguishably display a mass portion and a derived blood vessel identified in a medical image, thereby improving the visibility of the objects. Besides, this configuration enables the omission of the thinning process performed for each predetermined number of steps of the region growing. Further, it is possible to dispense with the calculation of the ratio of the number of voxels identified as the mass portion or the like to the total number of neighboring voxels. The comparison with the setting information can also be omitted.

(Modification 2)

As in the modification 1, for example, the identifying unit 5 may be configure to end the region growing after extending the region for a predetermined time set in advance from the center point CP without a determination as to whether the derived blood vessel region is reached and whether there is a branch. Alternatively, also in this modification 2, the identifying unit 5 may determine whether the derived blood vessel region is reached, but not determine whether there is a branch (steps S12 and S14). In the modification 2, the predetermined time is stored in advance. In this configuration, the identifying unit 5 acquires time information from a timer (not illustrated) when starting the second identification process. The identifying unit 5 compares the time information with information of the predetermined time stored in advance, and ends the region growing when it the predetermined time has elapsed.

In the sense of the end timing of the region growing, the mass portion and the derived blood vessel can be identified in also the modification 2. For example, the predetermined time is set in advance based on the size of a site to be examined in the subject, the distance to the derived blood vessel from the center point CP of the mass portion obtained by statistics, and the like. That is, based on the size and the distance, the number of steps to reach the derived blood vessel is obtained. The predetermined time is determined by multiplying the time taken for one step of the region growing by the number of steps. In this manner, based on the predetermined time set in advance, the process is terminated at the end timing of the region growing.

Accordingly, with this configuration also, an object with a complex shape can be identified in volume data. Thus, the image processing apparatus 10 can distinguishably display a mass portion and a derived blood vessel identified in a medical image, thereby improving the visibility of the objects. Besides, this configuration enables the omission of the thinning process performed for each predetermined number of steps of the region growing. Further, it is possible to dispense with the calculation of the ratio of the number of voxels identified as the mass portion or the like to the total number of neighboring voxels. The comparison with the setting information can also be omitted.

(Modification 3)

In the modification 1 or 2, after the region growing ends, the range identified so far may be displayed in the volume rendering image or the like to allow the user to edit the search region (add or reduce the region). That is, the image processing apparatus 10 displays the range identified in the modification 1 or 2 in the volume rendering image, and also an edit screen on the display D. The edit screen enables the addition or reduction of the range to be subjected to the region growing in a two-dimensional image through the operation unit C. The user enters a start point (the beginning) and an end point (the end) of additional region growing as a range of the region to be extended using the operation unit C. The designating unit 4 specifies the coordinates of the start point and those of the end point, and sends them to the identifying unit 5. The identifying unit 5 specifies the start point and the end point in the volume data. The identifying unit 5 starts the region growing from the start point thus specified, and ends it at the end point.

With this configuration, an object with a complex shape can be identified in volume data. Thus, the image processing apparatus 10 can distinguishably display a mass portion and a derived blood vessel identified in a medical image, thereby improving the visibility of the objects. Besides, this configuration enables the omission of the thinning process performed for each predetermined number of steps of the region growing. Further, it is possible to dispense with the calculation of the ratio of the number of voxels identified as the mass portion or the like to the total number of neighboring voxels. The comparison with the setting information can also be omitted.

Furthermore, even when the range of the region growing is required to be edited as a result of identifying the derived blood vessel in the modifications 1 and 2, the image processing apparatus 10 of the modification 3 allows the user to easily add or reduce the region.

(Modification 4)

Figure 8:
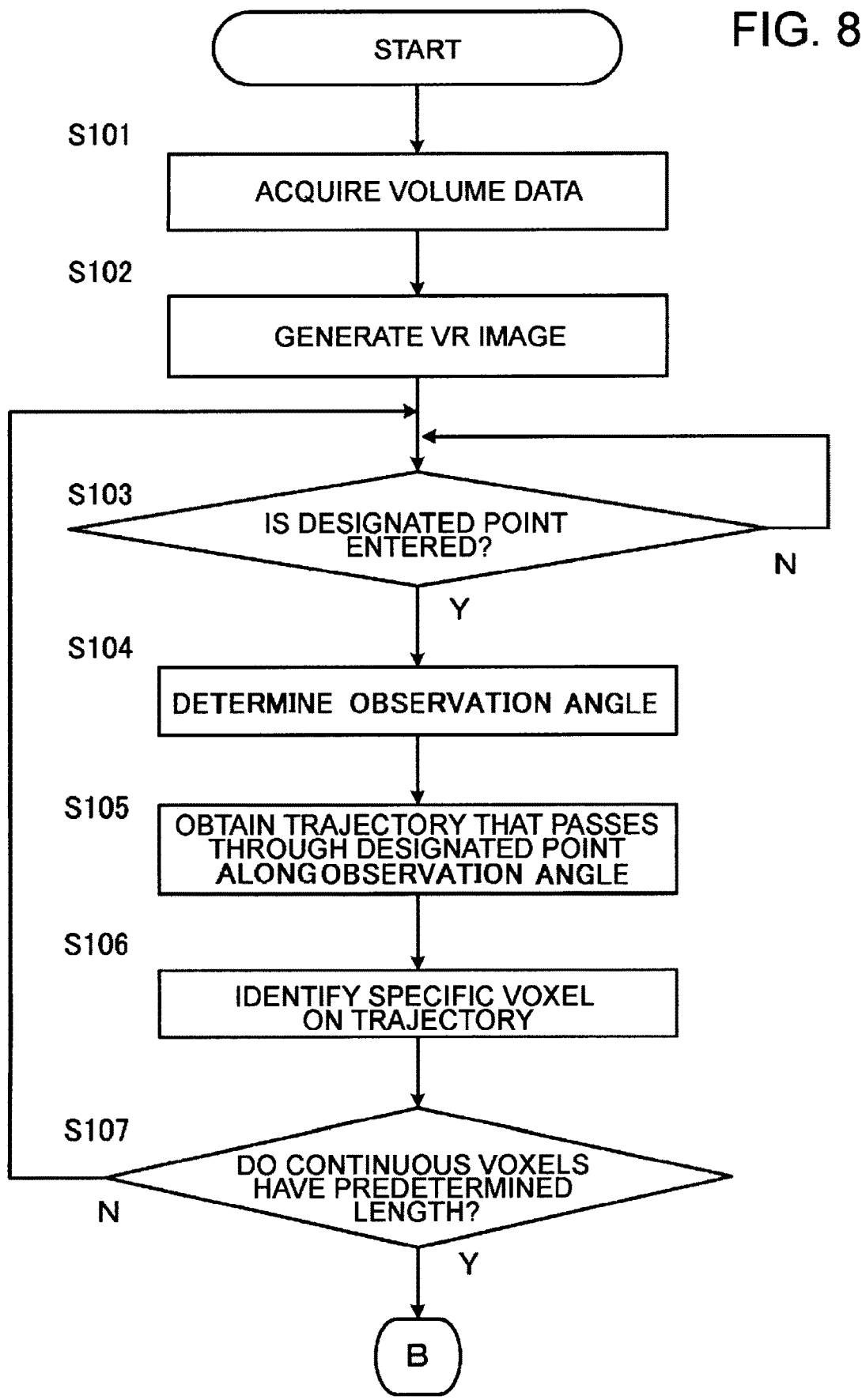
FIG. 8 is a flowchart of the operation of the image processing apparatus according to modification 4 of the first embodiment.
Figure 9:
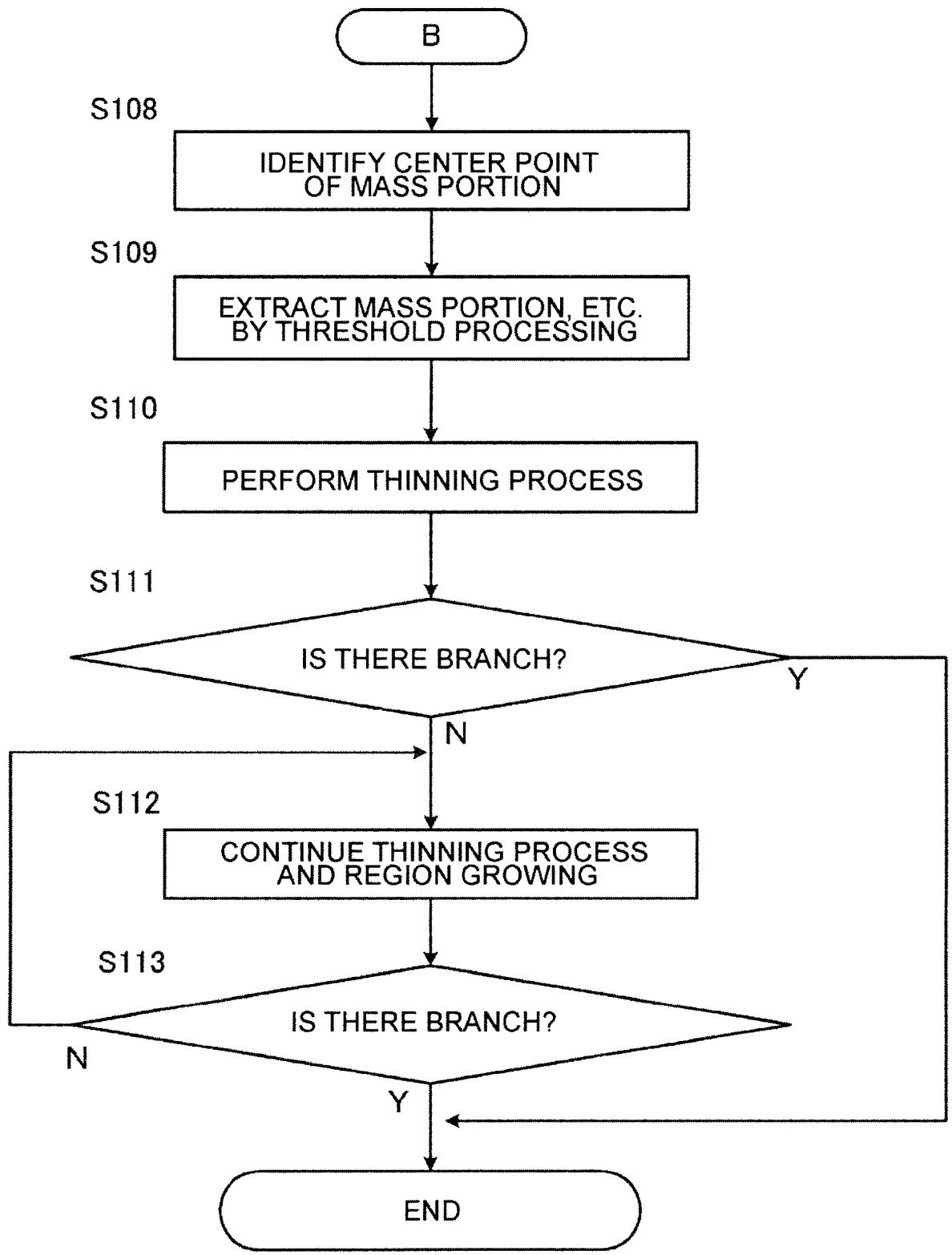
FIG. 9 is a flowchart of the operation of the image processing apparatus according to modification 4 of the first embodiment.

In this modification, after the center point CP of the mass portion is identified in the first identification process, the derived blood vessel is identified by threshold processing and the thinning process without the region growing. The operation of the modification 4 is described with reference to FIGS. 8 and 9. FIGS. 8 and 9 are flowcharts illustrating the outline of the operation of the image processing apparatus 10 according to the modification 4 of the first embodiment.

<Step S101>

Upon receipt of an operation signal from the operation unit C, the acquiring unit 1 requests the image storage device 30 for volume data. Consequently, the acquiring unit 1 receives the volume data from the image storage device 30, and at least temporarily stores it.

<Step S102>

The image processor 2, the image processing operation through an operation unit C, performs image processing related to generation of the two-dimensional image to the volume data. For example, based on various parameters such as observation angles set by the user, the image processor 2 performs volume rendering on the volume data to thereby generate a two-dimensional image. The display controller 3 displays the volume rendering image generated by the image processor 2 on the display D.

<Step S103>

The designating unit 4 determines whether operation is performed to designate a point, and also to confirm the designated point. The designating unit 4 repeats this determination until the operation is performed (No in step S103).

<Step S104>

Having determined that the operation is performed (Yes in step S103), the designating unit 4 sends the coordinate information of the designated point to the identifying unit 5. The identifying unit 5 acquires volume data related to the volume rendering image and the image processing conditions of the two-dimensional image processing. Then, the identifying unit 5 extracts the observation angle (projection direction) of the image with respect to the volume data from the image processing condition acquired.

<Step S105>

Next, based on the observation angle determined in S104, the identifying unit 5 obtains the trajectory RT that passes through the designated point DP in the observation angles in the volume data VD.

<Step S106>

The identifying unit 5 compares the setting information with the voxel values of voxels that the trajectory RT passes through. By this comparison, the identifying unit 5 identifies a region corresponding to a mass portion, a region of interest corresponding to a blood vessel, and other regions (see FIG. 3). As a result of the comparison, the identifying unit 5 obtains the coordinates of voxels with voxel values corresponding to the setting information among those that the trajectory RT passes through.

<Step S107>

The identifying unit 5 obtains the widths L1, L2, L3, . . . , and Ln of continuous voxels on the trajectory RT corresponding to a mass portion or the like, and determines the largest one of the widths. Further, the identifying unit 5 obtains the size (width, etc.) of the other mass portion relative to other sites (bone, etc.). The identifying unit 5 compares the largest width L1 with the relative size of the other mass portion. The identifying unit 5 determines whether the largest width L1 reaches the relative size. If the largest width L1 does not reach the relative size (No in step S107), the display controller 3 performs display control to prompt a user to enter the designated point again, and the process returns to step S103. This is because the designated point may be deviated from the region of the mass portion.

<Step S108>

Having determined that the largest width L1 reaches the predetermined size (Yes in step S107), the identifying unit 5 obtains the coordinates of the middle position of L1 based on the coordinates of the beginning and the end of L1 (L1/2). In this manner, the identifying unit 5 identifies the middle position obtained as the center point CP of the mass portion.

<Step S109>

The identifying unit 5 stores in advance the setting information of voxel values representing a mass portion and a blood vessel. The identifying unit 5 compares the setting information with the voxel values of voxels. With this, the identifying unit 5 can discriminate the voxels representing a mass portion or a blood vessel from other voxels. Besides, the identifying unit 5 extracts a mass portion including the center point CP and a derived blood vessel continuous with it. The derived blood vessel has a contour that is continuous with the contour of the mass portion.
<Step S110>
The identifying unit 5 performs the thinning process on the portion extracted in step S109 to obtain the center line of the region of the derived blood vessel extracted.
<Step S111>
The identifying unit 5 determines whether there is a branch in the center line obtained in step S110.
<Step S112>
Having determined that there is no branch in the center line obtained in step S110 (No in step S111), the identifying unit 5 continues the thinning process and the region growing of the derived blood vessel region.
<Step S113>
When determining that there is no branch in the center line in step S112, the identifying unit 5 repeats steps S112 and S113.
Having determined that there is a branch (Yes in step S111/S113), the identifying unit 5 ends the thinning process and the region growing of the derived blood vessel as the second identification process.
Based on the coordinate information obtained by the identification process, the extractor 6 associates the corresponding voxel with the first region information (mass region) and the second region information (derived blood vessel region). The extractor 6 sends the volume data associated with the region information to the identifying unit 5. The identifying unit 5 stores the volume data.
When operation is performed for displaying an image based on the volume data subjected to the above process, the image processor 2 specifies the derived blood vessel region based on the coordinate information of the first region information and that of the second region information associated with the volume data. The image processor 2 assigns a display mode set in advance to voxels in the region specified.
Incidentally, in the modification 4, after the derived blood vessel is identified by the thinning process, high transparency may be assigned to voxels except those of the mass portion and the derived blood vessel, or except those of the derived blood vessel. This substantially eliminates the voxels except those of the mass portion and the derived blood vessel, or except those of the derived blood vessel from the volume data.
The above modifications 1 to 3 may be applied to the modification 4. Specifically, the region growing may be ended according to predetermined conditions without a determination as to whether there is a branch.
With this configuration, an object with a complex shape can be identified in volume data. Thus, the image processing apparatus 10 can distinguishably display a mass portion and a derived blood vessel identified in a medical image, thereby improving the visibility of the objects.
(Controller)
In the first embodiment and the modifications 1 to 4, the image processing apparatus 10 includes a main controller (not illustrated). The main controller may be formed of, for example, CPU, ROM, RAM, or the like. The ROM stores a control program in advance. The CPU loads the control program into RAM and executes it as appropriate, thereby functioning as a main controller. In this manner, the main controller controls each unit of the image processing apparatus 10.

Second Embodiment

Figure 10:
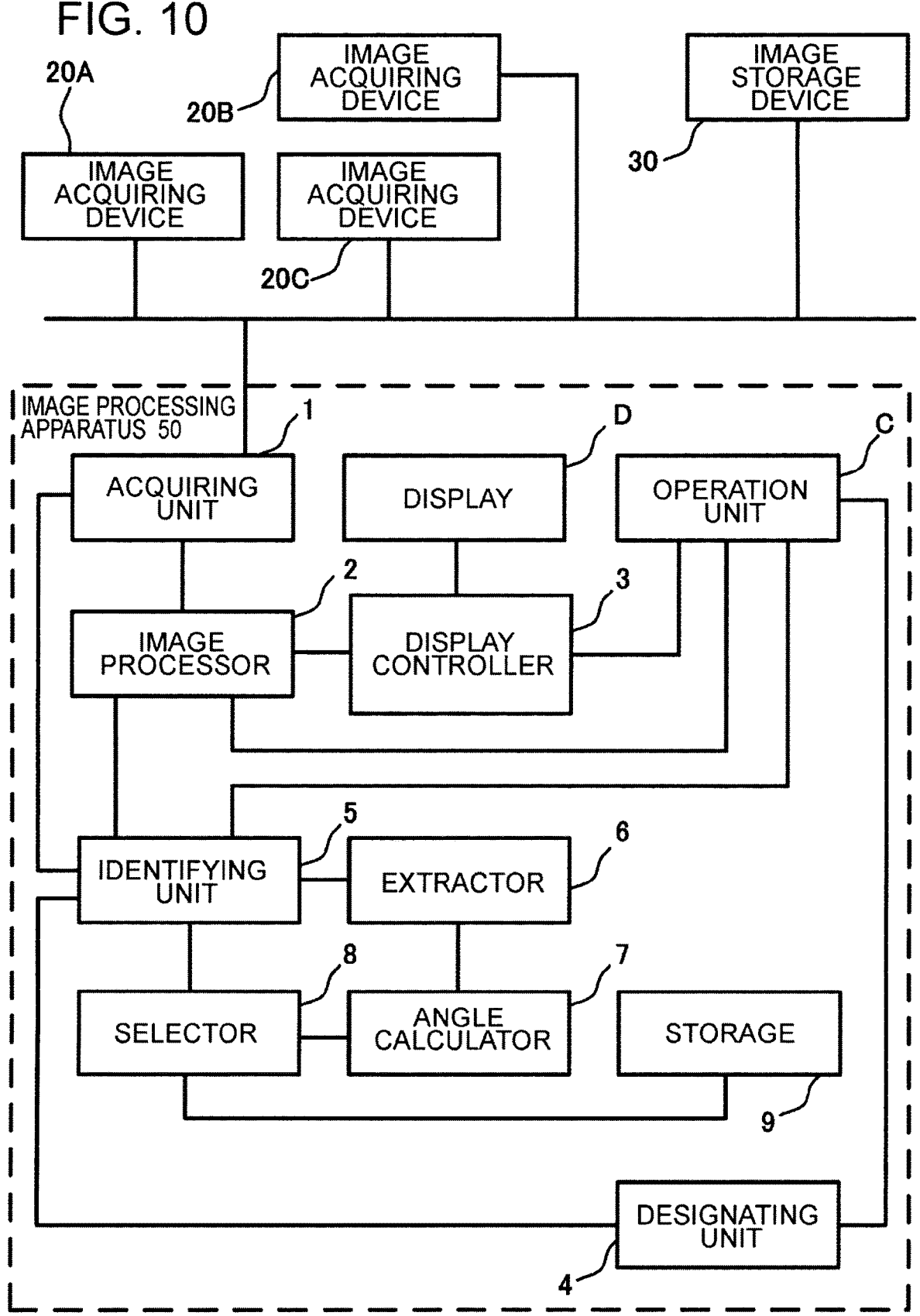
FIG. 10 is a block diagram of an image processing apparatus according to a second embodiment.

Next, with reference to FIG. 10, a description is given of a medical image processing system according to the second embodiment. FIG. 10 is a schematic block diagram illustrating a configuration of an image processing apparatus 50 of the second embodiment. Note that same reference numerals to those used in describing the first embodiment denote similar features in the second embodiment, and the same description is not repeated.
As illustrated in FIG. 10, the image processing apparatus 50 includes the display D, the operation unit C, the acquiring unit 1, the image processor 2, the display controller 3, the designating unit 4, the identifying unit 5, the extractor 6, an angle calculator 7, a selector 8, and a storage 9. Described below are a configuration of the angle calculator 7, the selector 8, and the storage 9 in the image processing apparatus 50, and a configuration associated therewith. The following description is given on the assumption that the second identification process has been completed, and that the extractor 6 has associated the voxels of the mass region with the first region information and the voxel of the derived blood vessel region with the second region information in the volume data.
(Angle Calculator)
The angle calculator 7 acquires the volume data after the processing by the extractor 6. Then, the angle calculator 7 specifies a mass region in the volume data based on the first region information. The angle calculator 7 also specifies each of derived blood vessel regions based on the second region information. The operation of the angle calculator 7 after this is explained in the first example and the second example.

First Example

Thereafter, the angle calculator 7 specifies the boundary between the mass region and the derived blood vessel region. In addition, the angle calculator 7 extracts the contour of the mass region and the derived blood vessel region. Based on the contour and the boundary thus extracted, the angle calculator 7 specifies a portion where the contour of the mass region is continuous with the contour of the derived blood vessel region. Then, the angle calculator 7 specifies a base of the derived blood vessel region based on information on the boundary between the mass region and the derived blood vessel region. Further, the angle calculator 7 specifies the protruding direction of the base by the thinning process or the like.
The angle calculator 7 obtains an angle between the protruding direction of the base of the derived blood vessel and the mass portion. The angle calculator 7 specifies this angle as the departure angle of the derived blood vessel from the mass portion.

Second Example

As the second example, another operation of the angle calculator 7 is described. The angle calculator 7 specifies the boundary between the mass region and each of the derived blood vessel regions. The angle calculator 7 specifies one of voxels in the boundary as the beginning of the derived blood vessel region. The angle calculator 7 specifies a branch of the derived blood vessel region, a point specified under other conditions (the modifications 1 to 4, etc.), or a point that the user has designated using the operation unit C as the end of the derived blood vessel region.

In addition, the angle calculator 7 obtains a line segment connecting the beginning and the end specified. Then, the angle calculator 7 obtains an angle between the line segment and part of the mass portion near the beginning. The angle calculator 7 specifies this angle as the departure angle of the derived blood vessel from the mass portion. For example, an angle between the line segment and the boundary between the mass region and the derived blood vessel region is specified as the departure angle Third Example As the third example, still another operation of the angle calculator 7 is described. The angle calculator 7 specifies the boundary between the mass region and each of the derived blood vessel regions. The angle calculator 7 specifies one of voxels of the boundary as a branch of the derived blood vessel region. Besides, the angle calculator 7 acquires information on the center point CP obtained by the first identification process of the identifying unit 5.

Further, the angle calculator 7 obtains the three-dimensional angle of the line connecting the branch and the center point CP in the volume data. The angle calculator 7 specifies this angle as the departure angle of the derived blood vessel from the mass portion.

(Storage)

The storage 9 stores display mode information corresponding to the departure angle. For example, the storage 9 stores the departure angle by dividing it into a plurality of ranges, such as first range, second range, . . . , and n-th range. The storage 9 stores a different display mode for each of the ranges. The display mode is the same as described in the first embodiment. That is, display color, transparency, and the like are determined by the display mode. The storage 9 is formed of a hard disk drive (HDD), a flash solid state drive (SSD), RAM, SSD, or the like.

(Selector)

The selector 8 receives information indicating each derived blood vessel and information on the departure angle of each derived blood vessel region associated with the derived blood vessel from the angle calculator 7. The information indicating the derived blood vessel is, for example, coordinate information indicating the blood vessel. For another example, the information indicating the derived blood vessel is the second region information (see first embodiment) associated by the extractor 6. However, in the second embodiment, the second region information is information (ID, etc.) that varies depending on the derived blood vessels.

The selector 8 retrieves information on the display mode for each derived blood vessel region from the storage 9 based on the information on the departure angle thereof. The selector 8 associates the display mode information thus retrieved with corresponding one of the derived blood vessel regions. For example, the display mode information is associated with voxel information. However, the information does not need to be associated with the voxel information. For example, the selector 8 may associate the display mode information with the second region information (ID, etc.) that identifies each derived blood vessel.

Upon completion of the process of associating the display mode information with the voxel in each derived blood vessel region, the selector 8 sends the volume data processed to the identifying unit 5. Incidentally, the mass region may be associated with a display mode that is not assigned in the process by the selector 8. Note that, preferably, the mass region is assigned a display mode clearly distinguishable from the display mode of the derived blood vessel region.

(Image Processor; Process of Varying Display Mode)

Described below is the process of varying the display mode of the mass region or the derived blood vessel region by the image processor 2. When operation is performed for displaying an image based on the volume data that has been subjected to the above process by the selector 8, the image processor 2 assigns a display mode set in advance to voxels in each derived blood vessel region based on the coordinate information of the voxels in the region associated with the volume data and the display mode information associated with the voxels. However, the display mode is not necessarily assigned to the voxel information. For example, the image processor 2 may assigns the display mode information to the second region information (ID, etc.) that identifies each derived blood vessel.

As the display mode, for example, display color may be set in advance. That is, the image processor 2 assigns red as display color to a first derived blood vessel region, and blue to a second derived blood vessel region. In this manner, the image processor 2 varies the display of a group of voxels in each derived blood vessel region according to the display mode associated thereto. The mass region may be assigned a different display mode which is not assigned to any of the voxels. Besides, the display mode may vary according to the transparency or a combination of the display color and transparency. Further, as in the first embodiment, the contour of each derived blood vessel region and that of the mass region may be displayed in a different display mode. The display mode may vary depending on combinations of the display color, transparency, and contour.

(Operation of the Image Processing Apparatus)

Figure 11:
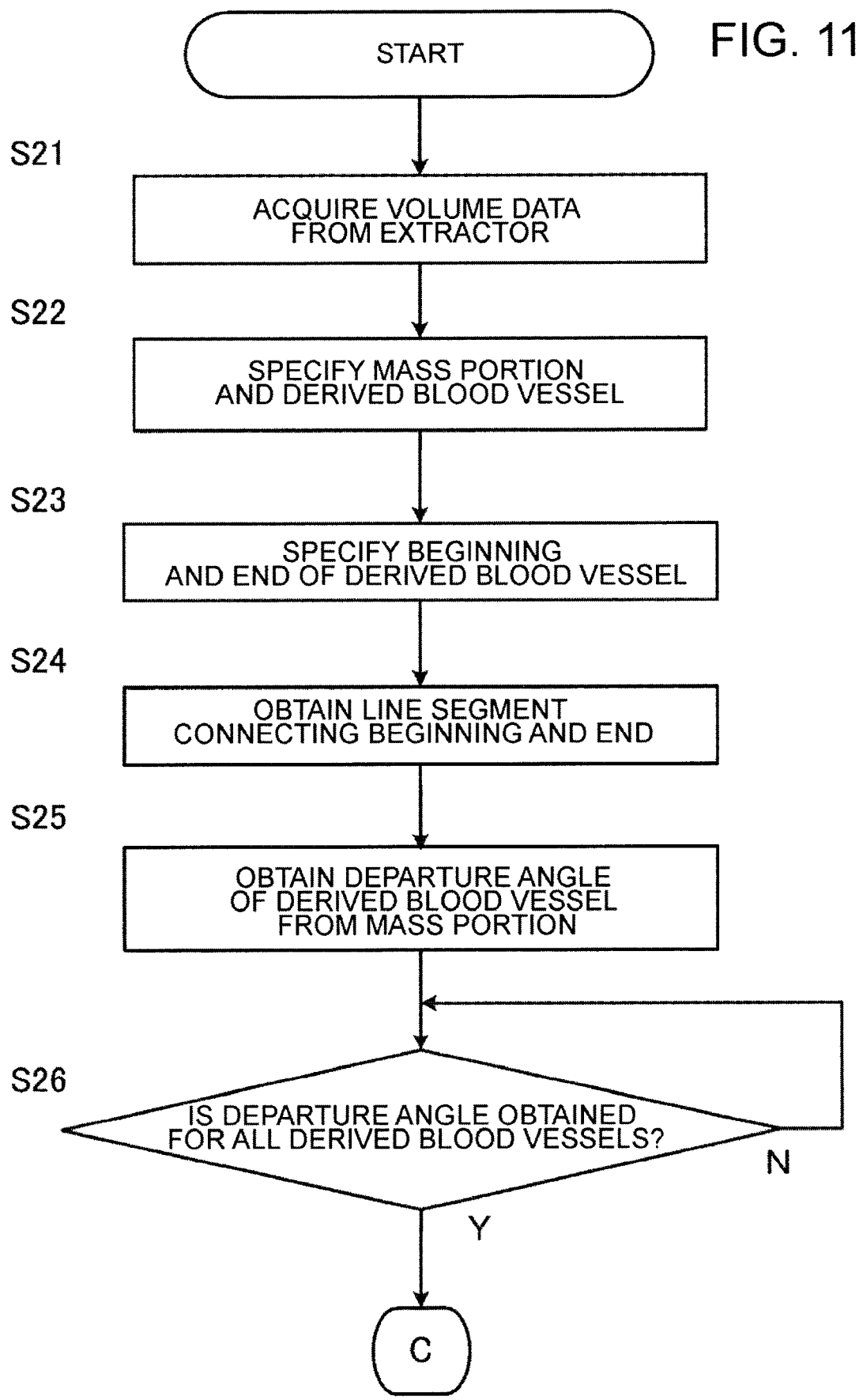
FIG. 11 is a flowchart of the operation of the image processing apparatus of the second embodiment.
Figure 12:
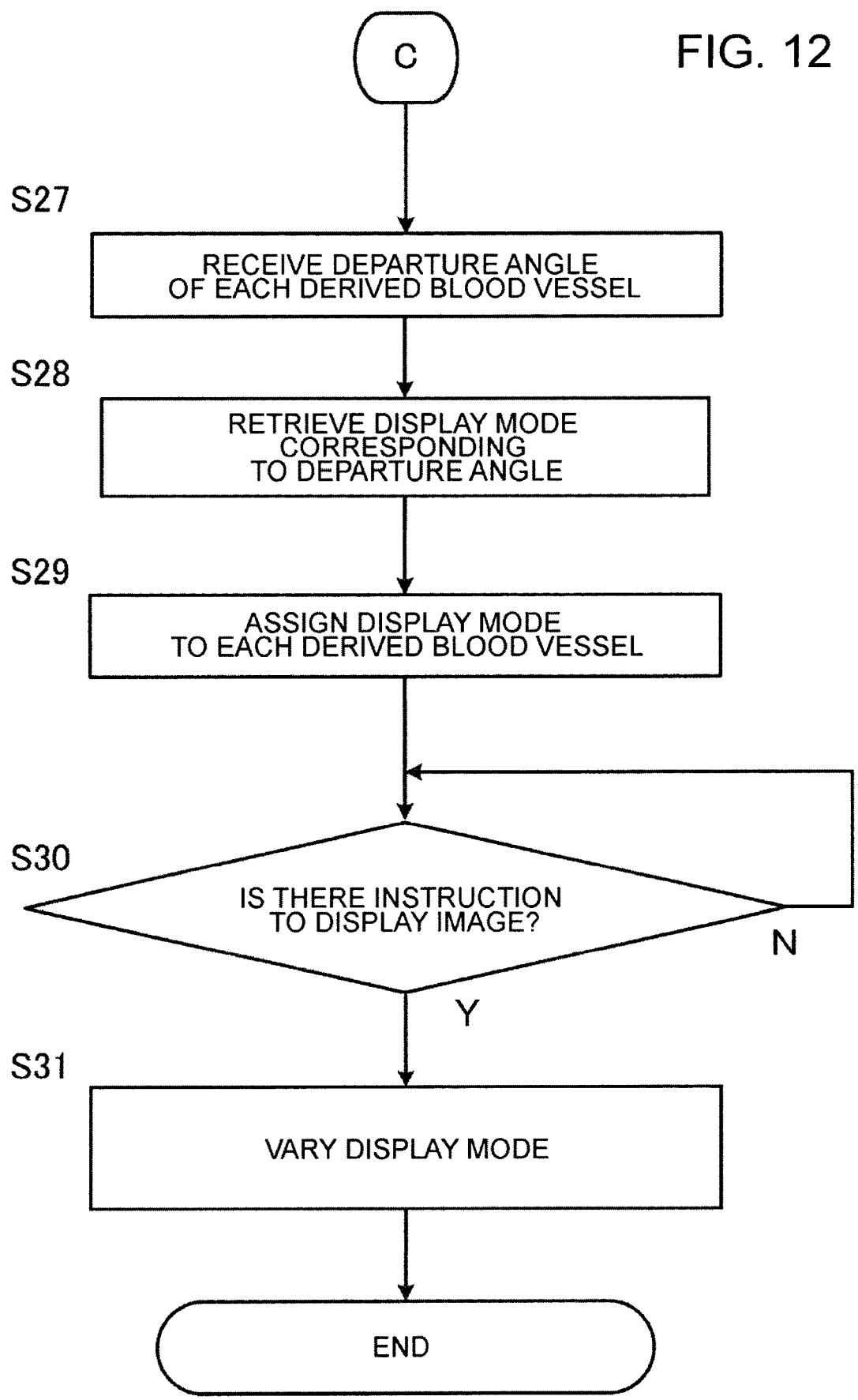
FIG. 12 is a flowchart of the operation of the image processing apparatus of the second embodiment.

Next, the operation of the image processing apparatus 50 according to the second embodiment is described with reference to FIGS. 11 and 12. FIGS. 11 and 12 are flowcharts illustrating the outline of the operation of the image processing apparatus 50 of the second embodiment. In the following, the calculation of the departure angle by the angle calculator 7 is described based on the above "second example".

<Step S21>

The angle calculator 7 acquires the volume data after the processing by the extractor 6.

<Step S22>

The angle calculator 7 specifies a mass region in the volume data based on the first region information. The angle calculator 7 also specifies each of derived blood vessel regions based on the second region information.

<Step S23>

The angle calculator 7 specifies the boundary between the mass region and each of the derived blood vessel regions. The angle calculator 7 specifies one of voxels in the boundary as the beginning of the derived blood vessel region with respect to each of the derived blood vessel regions specified. The angle calculator 7 specifies a branch of the derived blood vessel region or the like as the end of the derived blood vessel region.

<Step S24>

The angle calculator 7 obtains a line segment connecting the beginning and the end specified in step S23.

<Step S25>

The angle calculator 7 obtains an angle between the line segment obtained in step S24 and the boundary between the mass region and the derived blood vessel region specified in step S23 as the departure angle.

<Step S26>

The angle calculator 7 determines whether the departure angle is obtained for all the derived blood vessels. If there is a derived blood vessel for which the departure angle is yet to be obtained (No in step S26), the angle calculator 7 repeats steps S23 to S26.

<Step S27>

Having determined that the departure angle is obtained for all the derived blood vessels (Yes in step S26), the selector 8 receives information on the departure angle of the derived blood vessel region associated with each derived blood vessel from the angle calculator 7.

<Step S28>

The selector 8 retrieves display mode information for each derived blood vessel region from the storage 9 based on the information on the departure angle received in step S27.

<Step S29>

The selector 8 associates the display mode information retrieved in step S28 with corresponding one of the derived blood vessel regions.

<Step S30>

The image processor 2 determines whether operation is performed to instruct image display based on the volume data subjected to the above process by the selector 8. The image processor 2 waits until it receives operation related to an instruction for image display (No in step S26).

<Step S31>

When operation is performed to instruct image display, the image processor 2 assigns a display mode set in advance to voxels in each derived blood vessel region based on the identification information (coordinate information or the second region information) of the region associated with the volume data and the display mode information associated with the voxels.

According to the second embodiment, the image processing apparatus 50 acquires volume data including a mass portion and blood vessels derived from the mass portion as in the first embodiment. The image processing apparatus 50 generates a volume rendering image from the volume data. The image processing apparatus 50 receives an input of a designated point of the volume rendering image. Based on the designated point of the volume rendering image, the image processing apparatus 50 identifies a voxel (or a group of voxels) which is assumed to be the center point of the mass portion in the volume data. The image processing apparatus 50 performs region growing from the center point as the start point, and identifies a derived blood vessel region. The image processing apparatus 50 associates voxels identified in the volume data with information indicating the mass portion or the derived blood vessel.

With this configuration, an object in the volume data can be identified even if it has a complex shape like feeding arteries to a tumor, an inflow blood vessel to AVM, an outflow blood vessel from the neck or dome of an aneurysm, and the like. Thus, the image processing apparatus 10 can distinguishably display a mass portion and a derived blood vessel identified in a medical image, thereby improving the visibility of the objects.

Further, in the second embodiment, the image processing apparatus 50 obtains the departure angle of each derived blood vessel region from the mass portion in the volume data. The selector 8 retrieves the display mode with respect to each departure angle from the storage 9, and assigns the mode to each derived blood vessel region. For each derived blood vessel region, the image processor 2 varies the display mode depending on the departure angle. The mass portion may also be assigned a different display mode.

With this structure, the mass portion and the derived blood vessel can be further distinguishably displayed, thereby improving the visibility of the objects.

(Modification A)

A modification A of the second embodiment is described below. In the second embodiment, the display mode is associated with each predetermined range of the departure angle. However, the second embodiment is not limited to this. For example, the angle calculator 7 may first specify one derived blood vessel region, and uses this region as the first derived blood vessel region. The angle calculator 7 obtains the departure angle of the first derived blood vessel region from the mass portion as in the second embodiment, and uses this angle as the first departure angle.

Next, the angle calculator 7 specifies a derived blood vessel region other than the first derived blood vessel region. The derived blood vessel region is used as the second derived blood vessel region. The angle calculator 7 obtains the departure angle of the second derived blood vessel region from the mass portion as in the second embodiment. The departure angle is used as the second departure angle. In the same manner, the departure angle is obtained for other derived blood vessel regions.

Then, the selector 8 receives the first departure angle, the second departure angle, . . . , and the n-th departure angle from the angle calculator 7. The selector 8 is compares the first departure angle with the second departure angle. Alternatively, the selector 8 calculates the difference between the first departure angle and the second departure angle. When the comparison result or the difference is in a predetermined range, the selector 8 specifies the first derived blood vessel region as an inflow blood vessel to the mass portion. Further, the selector 8 specifies the second blood vessel region as the outflow blood vessel. The selector 8 performs the same process for the departure angle of other derived blood vessel regions.

For example, if the difference between the first departure angle and the second departure angle is in the range of 180°±15°, the selector 8 identifies one of derived blood vessel regions as the inflow blood vessel and the other as the outflow blood vessel. That is, regarding the first derived blood vessel region and the second derived blood vessel region which extend in substantially opposite directions, the selector 8 identifies one of them as an inflow blood vessel that connects to the artery, and the other as an outflow blood vessel that connects to the vein.

The image processor 2 performs image processing for varying the display mode between each derived blood vessel region identified as an inflow blood vessel and each derived blood vessel region identified as an outflow blood vessel. For example, the image processor 2 set the display color of the inflow blood vessel to red and that of the outflow blood vessel to blue.

In the modification A, an object with a complex shape can be identified in volume data. Thus, the image processing apparatus 50 can distinguishably display a mass portion and a derived blood vessel identified in a medical image, thereby improving the visibility of the objects. Further, in this modification, the user can clearly identify an outflow blood vessel and an inflow blood vessel with respect to a nidus of AVM, for example. Incidentally, each unit that performs the processes of the modification Third Embodiment Next, with reference to FIG. 13, a description is given of a medical image processing system according to the third embodiment. Note that the description of the same part as in the first embodiment is not repeated. The following describes only the content of processing after the first identification process, the second identification process, and the process of varying the display mode.

Figure 13:
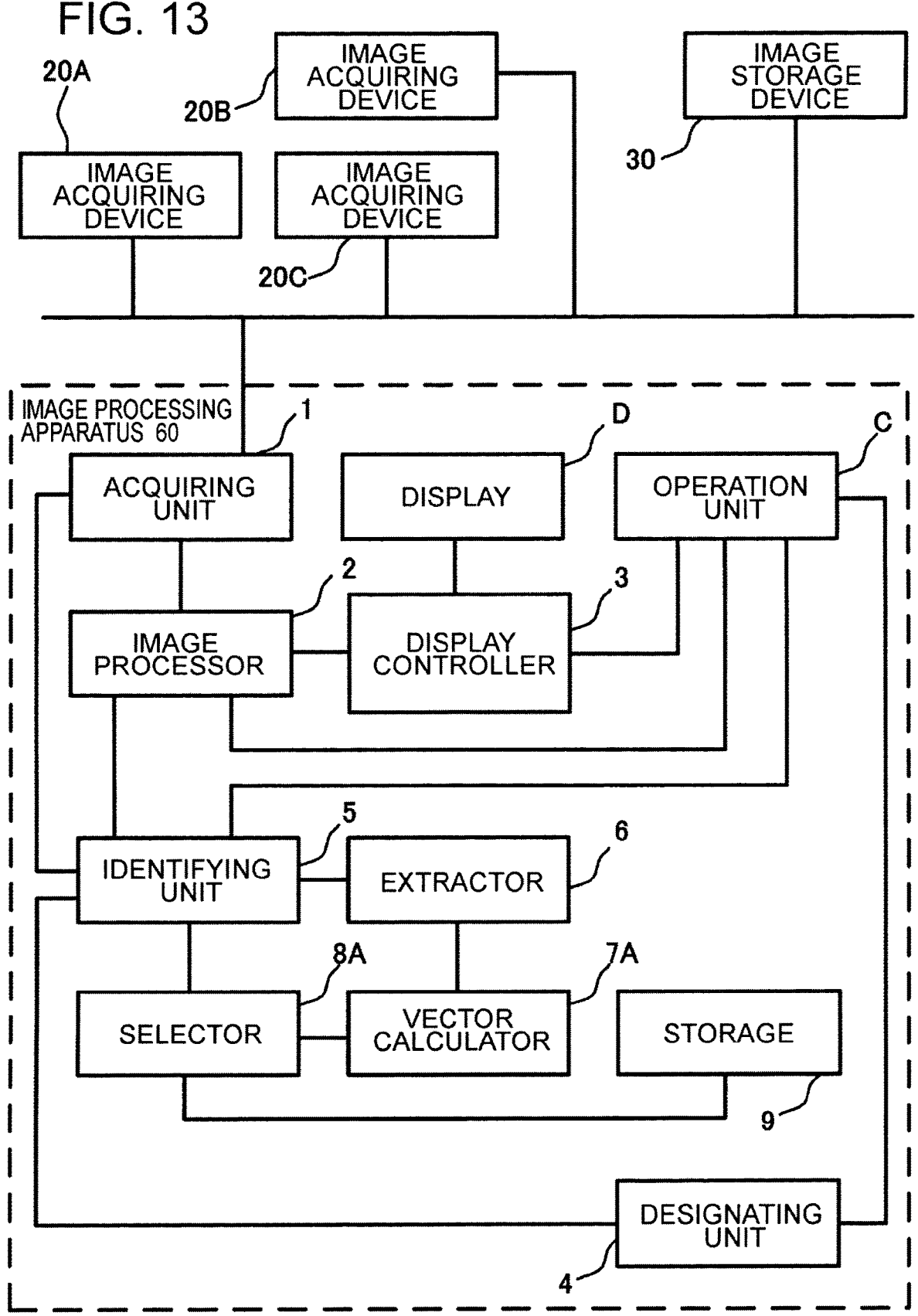
FIG. 13 is a block diagram of an image processing apparatus according to a third embodiment.

As illustrated in FIG. 13, an image processing apparatus 60 includes the display D, the operation unit C, the acquiring unit 1, the image processor 2, the display controller 3, the designating unit 4, the identifying unit 5, the extractor 6, a vector calculator 7A, a selector 8A, and a storage 9A. Described below are a configuration of the vector calculator 7A, the selector 8A, and the storage 9A in the image processing apparatus 60, and a configuration associated therewith. The following description is given on the assumption that the second identification process has been completed, and that the extractor 6 has associated the voxels of the mass region with the first region information and the voxel of the derived blood vessel region with the second region information in the volume data.

(Identifying Unit)

The identifying unit 5 acquires volume data processed by the extractor 6. Then, the identifying unit 5 identifies a branch portion (boundary portion) between the mass region and the derived blood vessel region in the volume data based on the first region information and the second region information. The identifying unit 5 identifies a branch portion with respect to each derived blood vessel region.

(Vector Calculator)

The vector calculator 7A specifies each derived blood vessel region in the volume data based on the second region information. The vector calculator 7A obtains the vector of the extending direction of the derived blood vessel region with respect to each branch portion identified by the identifying unit 5. Alternatively, the vector calculator 7A may obtain an angle between a line, which connects the branch portion and the center point specified by the first identification process of the identifying unit 5, and the extending direction of the derived blood vessel region as the departure angle.

(Storage)

The storage 9 stores display mode information corresponding to the extending direction. For example, the storage 9 stores the extending direction by dividing it into a plurality of ranges, such as first range, second range, . . . , and n-th range. The storage 9 stores a different display mode for each of the ranges. The display mode is the same as described in the first embodiment. That is, display color, transparency, and the like are determined by the display mode.

(Selector)

The selector 8A receives information on the vector of the extending direction associated with each derived blood vessel (coordinate information of each blood vessel) from the vector calculator 7A. Besides, with respect to each of derived blood vessel regions, the selector 8A retrieves display mode information from the storage 9 based on the information on the vector of the extending direction. The selector 8A associates the display mode information thus retrieved with corresponding one of the derived blood vessel regions. For example, the display mode information is associated with voxel information. Upon completion of the process of associating the display mode information with the voxel in each derived blood vessel region, the selector 8A sends the volume data processed to the identifying unit 5. Incidentally, the mass region may be associated with a display mode that is not assigned in the process by the selector 8A.

(Image Processor; Process of Varying Display Mode)

The image processor 2 varies the display mode of the mass region or the derived blood vessel region in the same manner as in the second embodiment.

According to the third embodiment, the image processing apparatus 60 acquires volume data including a mass portion and blood vessels derived from the mass portion as in the first embodiment. The image processing apparatus 60 generates a volume rendering image from the volume data. The image processing apparatus 60 receives an input of a designated point of the volume rendering image. Based on the designated point of the volume rendering image, the image processing apparatus 60 identifies a voxel (or a group of voxels) which is assumed to be the center point of the mass portion in the volume data. The image processing apparatus 60 performs region growing from the center point as the start point, and identifies a derived blood vessel region. The image processing apparatus 60 associates voxels identified in the volume data with information indicating the mass portion or the derived blood vessel.

With this configuration, an object in the volume data can be identified even if it has a complex shape like feeding arteries to a tumor, an inflow blood vessel to AVM, an outflow blood vessel from the neck or dome of an aneurysm, and the like. Thus, the image processing apparatus 60 can distinguishably display a mass portion and a derived blood vessel identified in a medical image, thereby improving the visibility of the objects.

Further, in the third embodiment, the image processing apparatus 60 obtains the vector of the extending direction of each of derived blood vessel regions from the mass portion in the volume data identified. Alternatively, the image processing apparatus 60 obtains an angle between a line, which connects the branch portion of the derived blood vessel region and the center point of the mass portion, and the extending direction of the blood vessel as the departure angle. The selector 8A retrieves display mode for each vector of the extending direction from the storage 9. The selector 8A assigns a display mode to each derived blood vessel region so that the display mode varies according to the departure angle. The mass region may also be assigned a different display mode.

With this configuration, derived blood vessels are each assigned a different display mode, and thereby displayed as classified. For example, in the image of AVM, inflow and outflow blood vessels can be clearly distinguishable. That is, in AVM, there are cases where the inflow blood vessel and the outflow blood vessel differ substantially by 180°. By obtaining the vector of the extending direction, they can be clearly distinguished from each other.

Fourth Embodiment

Figure 14:
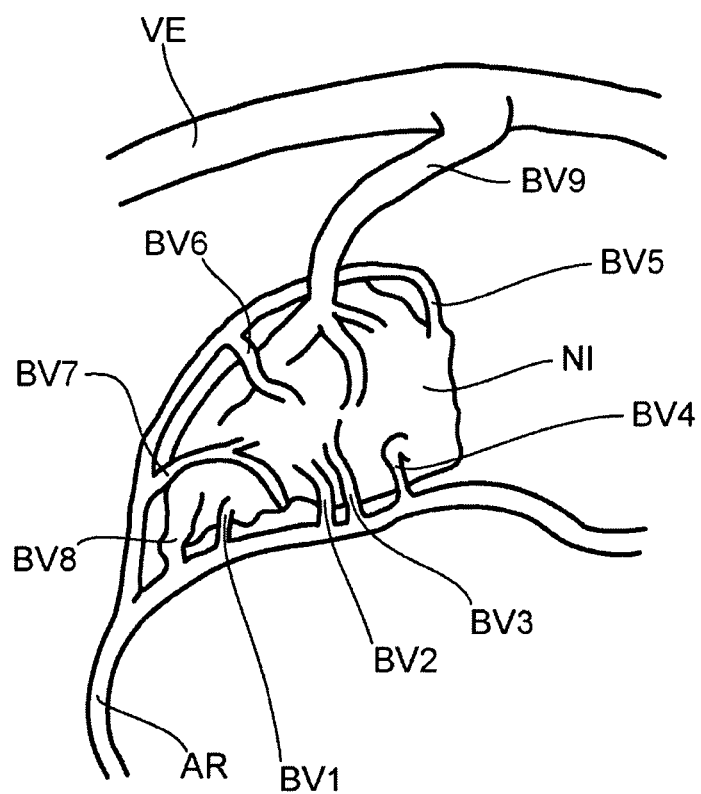
FIG. 14 is a schematic diagram illustrating the process of identifying a derived blood vessel according to a fourth embodiment.
Figure 15:
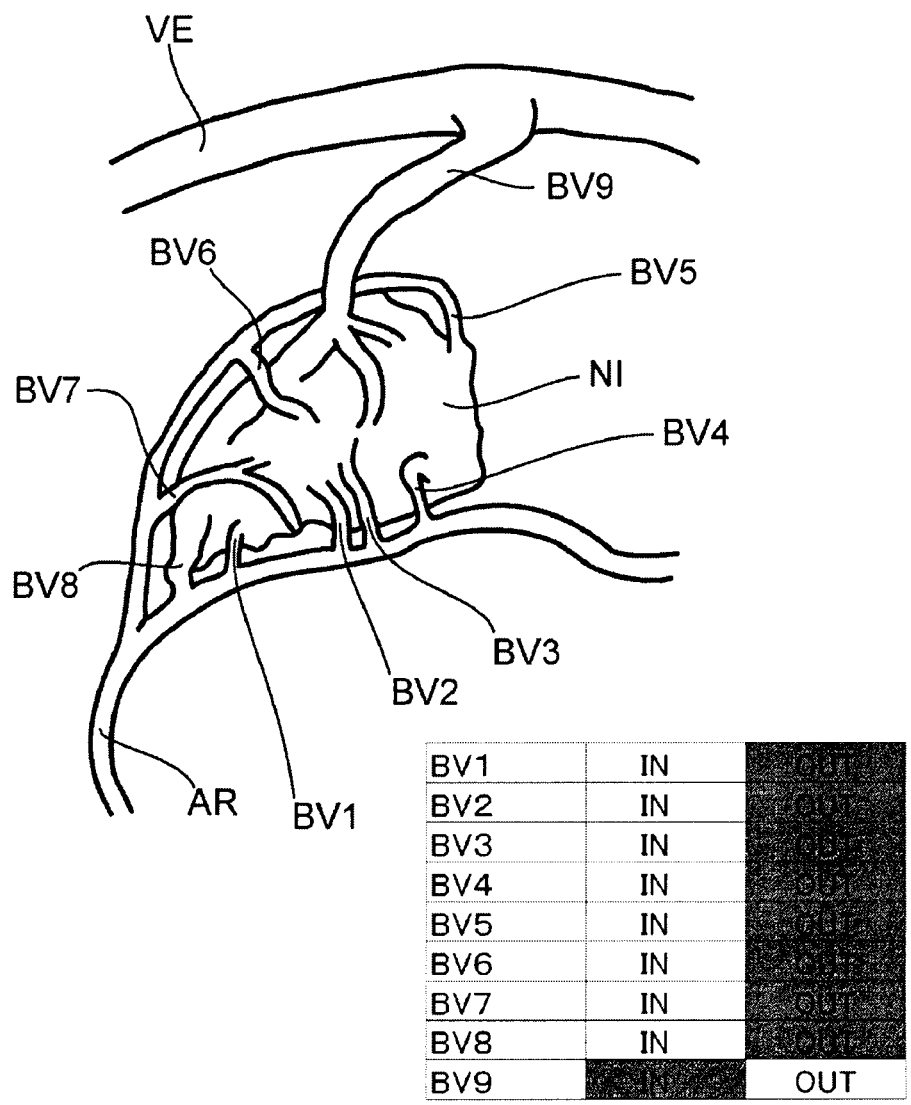
FIG. 15 is a first display example schematically illustrating a list screen of the fourth embodiment.
Figure 16:
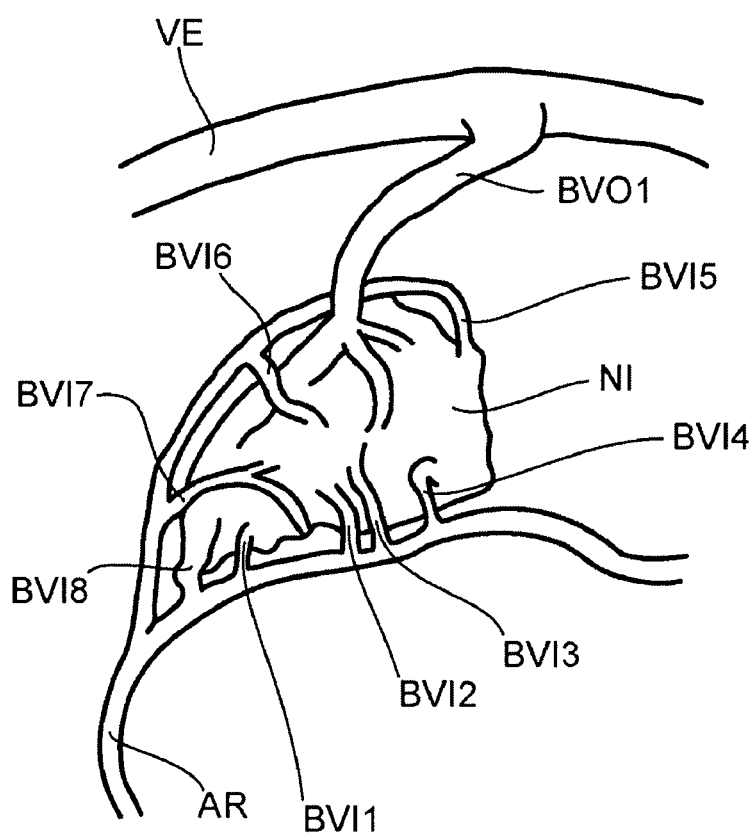
FIG. 16 is a schematic diagram illustrating the process of identifying a derived blood vessel in the fourth embodiment.
Figure 17:
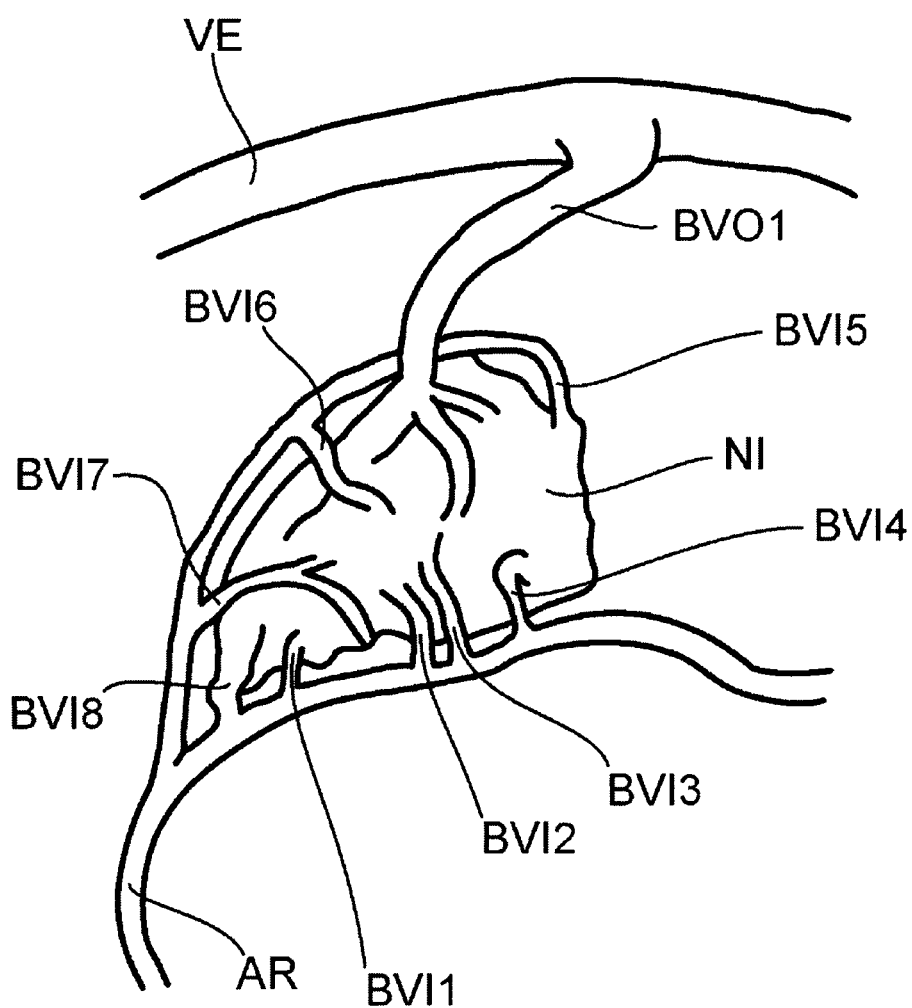
FIG. 17 is a second display example schematically illustrating the list screen of the fourth embodiment.

Next, with reference to FIGS. 14 to 17, a description is given of a medical image processing system according to the fourth embodiment. FIGS. 14 and 16 are schematic diagrams conceptually illustrating the process of identifying a derived blood vessel according to the fourth embodiment. FIG. 15 is a first display example illustrating the outline of a list screen of the fourth embodiment. FIG. 17 is a second display example illustrating the outline of the list screen of the fourth embodiment. Note that the description of the same part as in any of the first to third embodiments is not repeated. The following describes only the content of processing after the first identification process, the second identification process, and the process of identifying each derived blood vessel (assignment of the second region information to each blood vessel, etc.).
(Extractor)

First Example

As in the first embodiment, the extractor 6 receives coordinate information of voxels of a mass portion identified by the identifying unit 5, and coordinate information of voxels of derived blood vessels. In addition, the extractor 6 of the fourth embodiment identifies each derived blood vessel based on the coordinate information. Further, as illustrated in FIG. 14, the extractor 6 assigns identification information (BV1 to BV9 in FIG. 14, etc.) to each derived blood vessel. Note that mass portion NI in FIGS. 14 to 17 is schematic illustration of an example of AVM.

Besides, the extractor 6 creates a list as illustrated in FIG. 15 for each of derived blood vessels BV1 to BV9. The extractor 6 generates a composite image of the list created and an image of the region of interest including the mass portion NI and derived blood vessels BV1 to BV9. The composite image generated at this time is displayed such that each derived blood vessel is assigned an ID (see FIG. 15). The ID indicated for each derived blood vessel in the composite image is displayed with respect to the derived blood vessel in the list.

With respect to the ID list of derived blood vessels in the composite image, the user can enter whether each of the blood vessels is an inflow blood vessel or an outflow blood vessel. For example, when the user performs operation to enter the inflow blood vessel or the outflow blood vessel in the input field of the ID list of the derived blood vessels, the extractor 6 receives the operation, and controls, via the display controller 3, the display D to display the inflow blood vessel or the outflow blood vessel in the corresponding input field.

Second Example

When it is determined whether each of the derived blood vessels is an inflow blood vessel or an outflow blood vessel in the same manner as in the second or third embodiment, the extractor 6 may operate as follows.

For example, the extractor 6 receives the coordinate information of voxels in the mass portion identified by the identifying unit 5 and the coordinate information of voxels in each derived blood vessel. Further, the extractor 6 receives information obtained for each derived blood vessel indicating whether it is an inflow blood vessel or an outflow blood vessel (hereinafter, referred to as "blood flow information").

The extractor 6 of the fourth embodiment identifies each derived blood vessel based on the coordinate information and the blood flow information. Then, the extractor 6 determines whether each derived blood vessel is an inflow blood vessel or an outflow blood vessel based on the blood flow information. Further, as illustrated in FIG. 16, the extractor 6 assigns identification information (see BVI1 to BVI8 and BVO1 in FIG. 16) to each derived blood vessel.

The extractor 6 creates a list of inflow blood vessels BVI1 to BVI8 and an outflow blood vessel BVO1 as illustrated in FIG. 17. The extractor 6 generates a composite image of the list created and an image of the region of interest including the mass portion NI as well as the inflow blood vessels BVI1 to BVI8 and the outflow blood vessel BVO1. The composite image generated at this time is displayed such that each derived blood vessel is assigned an ID (see FIG. 17). The ID indicated for each derived blood vessel in the composite image is displayed with respect to each of the inflow blood vessels BVI1 to BVI8 and the outflow blood vessel BVO1 in the list.

Besides, the user can edit the ID list of the inflow blood vessels BVI1 to BVI8 and the outflow blood vessel BVO1 in the composite image. The term "edit" indicates that, for example, whether the blood vessel is an inflow or outflow blood vessel can be changed by user's operation. When the user determines that the classification as to inflow or outflow made by the selector or the like is not correct, he/she can edit the ID list. In this case, for example, the user clicks "Edit" button in the list displayed on the screen as illustrated in FIG. 17. In response to this operation, the extractor 6 may change the classification as to inflow or outflow for a derived blood vessel designated by the user so that the corrected list can be displayed.

The list may be edited in other ways. For another example, the user may drag an ID or the like of a derived blood vessel, which has been determined as an inflow blood vessel and displayed in a column for inflow blood vessels, and drops it on a column for outflow blood vessels in the list. For still another example, the user may designate the region of the image of a derived blood vessel drawn in the composite image rather than the list to edit the list.

In the second example, while the extractor 6 is described as being configured to determine whether each derived blood vessel is an inflow blood vessel or an outflow blood vessel based on the blood flow information, this is not a limitation. As in the second embodiment, the derived blood vessels may be classified by the range of their departure angles. For example, the extractor 6 may classify the derived blood vessels into groups as follows: a first group with the departure angle not less than 0° and less than 90° ($0°≤θ<90°$), a second group with the departure angle not less than 90° and less than 180° ($90°≤θ$ and $<180°$), a third group with the departure angle not less than 180° and less than 270° ($180°≤θ<270°$), and a fourth group with the departure angle not less than 270° and less than 360° ($270°≤θ$ and) $<360°$. In this case, the list may be displayed using this grouping as a major classification and ID of each derived blood vessel as a subdivision.

Third Example

In a third example of the fourth embodiment, the extractor 6 obtains information (a value, etc.) on at least any one of the length and diameter of the blood vessel, the blood flow rate, and the contrast agent concentration for each derived blood vessel. Further, the extractor 6 displays the information obtained with respect to each derived blood vessel ID in the list of the composite image.

If the length of the vessel is to be displayed, the extractor 6 calculates the length of each derived blood vessel based on the coordinate information of the contour or region of the derived blood vessel. The same applies to the case of the diameter of the blood vessel. The length or diameter is calculated using, for example, a core or a central line obtained by the thinning process for each derived blood vessel.

If the contrast agent concentration is to be displayed, the extractor 6 compares information of a voxel value that indicates a contrast agent and the voxel value of each voxel corresponding to the coordinate information of each derived blood vessel in the volume data to obtain the concentration of the contrast agent for the derived blood vessel. The information of the voxel value indicating the contrast agent is not a constant value and includes a voxel value in a predetermined range corresponding to the concentration of the contrast agent. Besides, the information on the voxel value is stored in advance. Thus, the extractor 6 can obtain the contrast agent concentration based on the voxel value of each voxel included in the derived blood vessel region.

The extractor 6 displays the information on at least any one of the length and diameter of the blood vessel, the blood flow rate, and the contrast agent concentration obtained for each derived blood vessel correspondingly to ID of the derived blood vessel in the list of the composite image as illustrated in FIG. 15 or 17. For example, the list includes a length field, a diameter field, and a concentration field corresponding to the ID field. In the list of the derived blood vessels, the items of the vessel length, diameter and the contrast agent concentration may be appropriately displayed according to the user's selection.

Fourth Example

In the first to third examples described above, the extractor 6 is configured to create a composite image of a list and an image indicating the mass portion NI and derived blood vessels. However, the list need not necessarily be created. For example, if ID is displayed for each derived blood vessel in the image (morphology image, etc.) indicating the mass portion NI and derived blood vessels, the user can designate one of the derived blood vessels to change the display mode thereof. In response to the user's operation to change the display mode, the display controller 3 controls the display D to display the derived blood vessel designated in the selected display mode. This can be used to highlight a derived blood vessel to be treated first in the image.

Fifth Example

In the same manner as in the fourth example, in the fifth example, the list is not created. The extractor 6 of the fifth example creates at least identification ID for each derived blood vessel. In the fifth example, when the image indicating the mass portion NI and derived blood vessels is displayed, the user can move a pointer displayed in the image to a region indicating any one of the blood vessels using a pointing device of the operation unit C or the like. When the pointer is displayed superimposed on the derived blood vessel, the extractor 6 creates an image in which ID of the derived blood vessel is displayed in a pop-up form or the like. The display controller 3 displays the image on the display D.

In the fifth example, if the extractor 6 acquires other information, the information may be displayed with ID. Examples of the other information include the length and diameter of the blood vessel, the blood flow rate, and the contrast agent concentration for each derived blood vessel.

Sixth Example

In the sixth example, the extractor 6 obtains the concentration of the contrast agent for each derived blood vessel as described above. The contrast agent concentration of the derived blood vessel at a predetermined time represents the amount of blood flow from the artery ar (see FIGS. 14 to 17). If a large amount of blood flow is received from the artery ar, it is expected that the derived blood vessel exerts a large influence. Taking this into consideration, in the sixth example, the extractor 6 generates an image in which a derived blood vessel with the highest concentration is highlighted. The display controller 3 displays the image on the display D. This can be used to highlight a derived blood vessel to be treated first in the image According to the fourth embodiment, the image processing apparatus acquires volume data including a mass portion and blood vessels derived from the mass portion as in the first embodiment. The image processing apparatus generates a volume rendering image from the volume data. The image processing apparatus receives an input of a designated point of the volume rendering image. Based on the designated point of the volume rendering image, the image processing apparatus identifies a voxel (or a group of voxels) which is assumed to be the center point of the mass portion in the volume data. The image processing apparatus performs region growing from the center point as the start point, and identifies a derived blood vessel region. The image processing apparatus associates voxels identified in the volume data with information indicating the mass portion or the derived blood vessel.

With this configuration, an object in the volume data can be identified even if it has a complex shape like feeding arteries to a tumor, an inflow blood vessel to AVM, an outflow blood vessel from the neck or dome of an aneurysm, and the like. Thus, the image processing apparatus can distinguishably display a mass portion and a derived blood vessel identified in a medical image, thereby improving the visibility of the objects.

Further, the image processing apparatus of the fourth embodiment identifies each derived blood vessel to provide the user with predetermined information. For example, in the first to third examples, information related to derived blood vessels identified (classification as to outflow or inflow, etc.) is displayed in a list. In the fourth example, ID of each derived blood vessel is displayed in a morphology image or the like, and the display mode can be changed in response to the selection of ID. In the fifth example, information related to a derived blood vessel identified is displayed in a pop-up form in response to a mouse operation or the like. In the third and fifth examples, the user can be provided with various types of information about derived blood vessels identified. In any of the first to sixth examples, by highlighting a particular derived blood vessel, the display can be applied to the subsequent treatment.

Note that features or characteristics of the first to sixth examples of the fourth embodiment may be combined in any suitable manner.

Fifth Embodiment

Next, a description is given of a medical image processing system according to the fifth embodiment. Note that the description of the same part as in the first embodiment is not repeated. The following describes only the content of processing after the first identification process, the second identification process, and the process of varying the display mode.

An X-ray Angio system may sometimes be required to display a three-dimensional road map by user's instruction before acquiring fluoroscopic X-ray images. For example, when the user presses a three-dimensional road map button, the controller of the X-ray Angio system displays a screen for selecting an image to be superimposed on a fluoroscopic X-ray image on the display. The user selects volume data to be superimposed on the selection screen.

Examples of the volume data include three-dimensional DSA data, three-dimensional DA data, CTA data, MRA data, and the like. In response to user's selection, the X-ray Angio system requests the image processing apparatus 10 (or the image processing apparatus 50 or the image processing apparatus 60, the same applies hereinafter) for the volume data.

The image processing apparatus 10 sends the volume data associated with a patient ID or an examination ID related to the request to the X-ray Angio system. The volume data has been subjected to the process of varying the display mode according to any one of the first to fourth embodiments or the modifications thereof.

At this time, the X-ray Angio system may extract a mass region and a derived blood vessel region based on coordinate information of the mass region and that of the derived blood vessel region associated with the volume data. For example, the transparency of parts other than the mass region and the derived blood vessel region is set at 100%.

Further, in the X-ray Angio system, the controller or the like performs image processing based on the volume data from which the mass region and the derived blood vessel region have been extracted. Examples of the image processing include voxel value projection such as maximum intensity projection, minimum intensity projection, and average intensity projection, MPR processing, volume rendering, surface rendering, and the like. By the image processing, data is generated of a two-dimensional image related to a specified angle in the X-ray Angio system. The specified angle refers to an observation angle appropriate in the generation of a composite image (described later).

Upon receipt of an instruction to acquire fluoroscopic X-ray images, the imaging mechanism of the X-ray Angio system acquires data of fluoroscopic X-ray images under the control of the controller. This acquisition is continuously or intermittently performed during catheterization (embolization). The data of fluoroscopic X-ray images acquired is stored in the storage of the X-ray Angio system.

After the acquisition of fluoroscopic X-ray images starts, and the user presses the three-dimensional road map button, the controller retrieves the data of the two-dimensional image related to the specified angle. In this image, the display mode of the mass region and the derived blood vessel region differs from that of the other parts. In some cases, only the mass region and the derived blood vessel region are extracted and displayed. Hereinafter the image is referred to as "road map image".

An image combining unit of the X-ray Angio system combines the roadmap image and the fluoroscopic X-ray image such that anatomical locations in the two images substantially match. For example, the image combining unit is configured to match the locations according to a position shift amount calculated in advance by a position shift calculator. This generates data of the composite image. The composite image is displayed on the display. The composite image may sometimes contain a guide wire region (or a catheter region) derived from the fluoroscopic X-ray image.

In this manner, the mass region and the derived blood vessel region are displayed in a display mode different from that of the other parts in the composite image. Accordingly, it can be easily determined if the catheter has entered a blood vessel of interest, or it has entered another vessel.

Note that, during the acquisition of fluoroscopic X-ray images, the imaging angle of the C-arm of the imaging mechanism may be changed in the X-ray Angio system. When the imaging angle is changed, data of a road map image that substantially matches the imaging angle changed is generated based on the volume data. Further, the composite image of the road map image and the fluoroscopic X-ray image is generated and displayed by the controller or the like. Thus, even when the imaging angle of the C-arm is changed, according to this embodiment, a fluoroscopic X-ray image and a roadmap image corresponding to the imaging angle changed are combined and a composite image thereof can be displayed.

According to the fifth embodiment, the image processing apparatus acquires volume data including a mass portion and blood vessels derived from the mass portion as in the first embodiment. The image processing apparatus generates a volume rendering image from the volume data. The image processing apparatus receives an input of a designated point of the volume rendering image. Based on the designated point of the volume rendering image, the image processing apparatus identifies a voxel (or a group of voxels) which is assumed to be the center point of the mass portion in the volume data. The image processing apparatus performs region growing from the center point as the start point, and identifies a derived blood vessel region. The image processing apparatus associates voxels identified in the volume data with information indicating the mass portion or the derived blood vessel.

With this configuration, an object in the volume data can be identified even if it has a complex shape like feeding arteries to a tumor, an inflow blood vessel to AVM, an outflow blood vessel from the neck or dome of an aneurysm, and the like. Thus, the image processing apparatus can distinguishably display a mass portion and a derived blood vessel identified in a medical image, thereby improving the visibility of the objects.

According to the first to fifth embodiments and the modifications thereof, the image processing apparatus can identify an object in volume data even if it has a complex shape. Therefore, the image processing apparatus is capable of distinguishably display a mass portion and a derived blood vessel identified in a medical image, thereby improving the visibility of the objects.

Further, some or all of the features of the first to fifth embodiments and modifications thereof can be combined in all possible ways. In addition, the image acquiring device and the medical image processing apparatus may be integrated in one apparatus. In this case, in addition to the constituent parts of the image processing apparatus 10 (50, 60), the apparatus includes a scanner configured to scan a subject to acquire acquisition data indicating the status of a three-dimensional region including a mass portion and derivation blood vessels in the subject. The apparatus further includes a volume data generator configured to generate volume data based on the acquisition data. Besides, the image processing apparatus 10 (50, 60) and the image acquiring device have a common display. The integrated apparatus of the image acquiring device and the medical image processing apparatus corresponds to an example of "medical image diagnostic apparatus".

While certain embodiments have been described, these embodiments have been presented by way of example only, and are not intended to limit the scope of the inventions. Indeed, the novel embodiments described herein may be embodied in a variety of other forms; Further, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising processing circuitry configured to:
   acquire volume data indicating a state of a three-dimensional region including a mass portion and blood vessels derived from the mass portion in a subject;
   specify a region corresponding to the mass portion and the blood vessels in the volume data as a region of interest;
   identify the mass portion, a center point of the mass portion, and each of the blood vessels in the region of interest;
   assign a different display mode to at least one of the mass portion and the blood vessels;
   identify a mass region representing the mass portion and a blood vessel region corresponding to the blood vessels based on a region growing process for extending a region from the center point of the mass portion in the volume data by iteratively appending to the center point of the mass portion a mass voxel of a connected region that belongs to the mass portion by determining that the mass voxel has a voxel value within a range of setting information for the mass portion;
   iteratively extending the region by the region growing process by performing a thinning process for each iteration of the extending the region by the region growing process;
   identify whether the region extends in less than all directions based on a number of voxels corresponding to the mass region and the blood vessel region among all neighboring voxels;
   identify, when the region extends in less than all directions, a blood vessel voxel that is thinned by the thinning process in an image of a blood vessel as a center line of the blood vessel, the blood vessel extending in directions in which the region extends in the blood vessel region;
   determine whether there is a branch in the blood vessel by determining that there is a branch in the center line of the blood vessel; and
   end the region growing process when there is a branch in the blood vessel.

2. The medical image processing apparatus of claim 1, wherein the processing circuitry is further configured to create a list of the blood vessels identified.

3. The medical image processing apparatus of claim 2, wherein the processing circuitry is further configured to obtain at least one of length, diameter, and contrast agent concentration with respect to the each of the blood vessels identified, and display in the list the at least one of length, diameter, and contrast agent concentration obtained.

4. The medical image processing apparatus of claim 1, wherein the processing circuitry is further configured to:
   generate a two-dimensional image including the mass portion and the blood vessels based on the volume data;
   receive a designated point for the mass portion in the two-dimensional image; and
   identify substantially the center point of the mass portion based on a positional relationship between the two-dimensional image and the volume data and a position of the designated point in the volume data.

5. The medical image processing apparatus of claim 1, wherein the processing circuitry is further configured:
   store a threshold to identify a voxel corresponding to the mass portion or a blood vessel in the region growing;
   obtain a value indicating a change in voxel value of neighboring voxels searched in the region growing; and
   identify the voxel corresponding to the mass portion or the blood vessel based on the threshold and the value indicating a change.

6. The medical image processing apparatus of claim 1, wherein the processing circuitry is further configured to obtain a departure angle of the each of the blood vessels from the mass portion,
   wherein the medical image processing apparatus further comprises a storage configured to store display mode information corresponding to the departure angle, and
   wherein the processing circuitry is further configured to:
      retrieve, from the storage, the display mode information corresponding to the departure angle obtained; and
      assign the different display mode to a blood vessel region corresponding to the blood vessel having the departure angle based on the display mode information.

7. The medical image processing apparatus of claim 6, wherein the processing circuitry is further configured to specify a base of the blood vessel on a side of the mass portion in the region of interest, and obtain as the departure angle an angle between part of the mass portion continuous with the base and the base.

8. The medical image processing apparatus of claim 7, wherein the processing circuitry is further configured to specify beginning of the blood vessel on the side of the mass portion and end thereof in the region of interest, and obtain as the departure angle an angle between part of the mass portion near the beginning and a line segment connecting the beginning and the end.

9. The medical image processing apparatus of claim 6, wherein the processing circuitry is further configured to:
   identify a branch between the blood vessel region and the mass portion; and
   obtain a three-dimensional angle of a line connecting the branch and a substantial center of the mass portion as the departure angle.

10. The medical image processing apparatus of claim 6, wherein the processing circuitry is further configured to:
   compare departure angles of the blood vessels to classify the blood vessels; and
   vary the display mode according to the blood vessels classified.

11. The medical image processing apparatus of claim 6, wherein the processing circuitry is further configured to:
   obtain a difference between a first departure angle of one blood vessel and a second departure angle of another blood vessel; and
   specify the blood vessel corresponding to the first departure angle as an inflow blood vessel to the mass portion, and the other blood vessel as an outflow blood vessel, when the difference is within a predetermined range.

12. The medical image processing apparatus of claim 6, wherein the processing circuitry is further configured to:
   compare departure angles of the blood vessels to specify a first blood vessel and a second blood vessel which extend in substantially opposite directions; and
   specify one of the first blood vessel and the second blood vessel as an inflow blood vessel and another as an outflow blood vessel based on the departure angles thereof.

13. The medical image processing apparatus of claim 12, wherein the processing circuitry is further configured to display the inflow blood vessel and the outflow blood vessel in different colors.

14. The medical image processing apparatus of claim 1, wherein the processing circuitry is further configured to display the mass portion and the blood vessels in at least either one of different color and different transparency from other parts as the different display mode.

15. The medical image processing apparatus of claim 1, wherein the processing circuitry is further configured to extract a contour of the mass portion and the blood vessels and highlight the contour to display at least one of blood vessel regions each corresponding to one of the blood vessels in the different display mode.

\* \* \* \* \*